(12) United States Patent
Brugidou et al.

(10) Patent No.: US 9,045,530 B2
(45) Date of Patent: Jun. 2, 2015

(54) MEANS FOR THE TRANSIENT PRODUCTION IN PLANTS OF RECOMBINANT PROTEINS THAT CAN BE USED IN PARTICULAR IN PROPHYLAXIS AND IN THERAPEUTICS

(75) Inventors: Christophe Brugidou, Pignan (FR); Jean-Loup Lemesre, Saint Martin de Londres (FR); Denis Fargette, Castelnau le Lez (FR); Drissa Sereme, Ouagadougou (BF); Moumouni Konate, Ouagadougou (BF); Gnissa Konate, Ouagadougou (BF)

(73) Assignees: INSTITUT DE RECHERCHE POUR LE DEVELOPPEMENT, Marseilles (FR); INSTITUT DE L'ENVIRONNEMENT ET DE RECHERCHES AGRICOLES, Ouagadougou (BF)

( * ) Notice: Subject to any disclaimer, the term of this patent is extended or adjusted under 35 U.S.C. 154(b) by 0 days.

(21) Appl. No.: 13/699,014

(22) PCT Filed: May 26, 2011

(86) PCT No.: PCT/IB2011/052288
§ 371 (c)(1),
(2), (4) Date: Dec. 7, 2012

(87) PCT Pub. No.: WO2011/148331
PCT Pub. Date: Dec. 1, 2011

(65) Prior Publication Data
US 2013/0085268 A1    Apr. 4, 2013

(30) Foreign Application Priority Data
May 26, 2010    (FR) .................................... 10 02204

(51) Int. Cl.
| | | |
|---|---|---|
| C12N 15/87 | (2006.01) |
| C07K 14/00 | (2006.01) |
| C07K 14/44 | (2006.01) |
| C12N 15/82 | (2006.01) |

(52) U.S. Cl.
CPC ................. C07K 14/00 (2013.01); C07K 14/44 (2013.01); C12N 15/8257 (2013.01)

(58) Field of Classification Search
None
See application file for complete search history.

(56) References Cited

U.S. PATENT DOCUMENTS

| | | |
|---|---|---|
| 2008/0026467 A1 | 1/2008 | Lemesre et al. |
| 2008/0131444 A1 | 6/2008 | Brugidou et al. |
| 2009/0162832 A1 | 6/2009 | Brugidou et al. |
| 2009/0214595 A1 | 8/2009 | Lemesre et al. |

FOREIGN PATENT DOCUMENTS

| | | |
|---|---|---|
| WO | WO-01/38512 A2 | 5/2001 |
| WO | WO-2005/051989 A2 | 6/2005 |
| WO | WO-2006/042979 A1 | 4/2006 |
| WO | WO-2006/072742 A2 | 7/2006 |
| WO | WO-2006/085011 A1 | 8/2006 |

Primary Examiner — Brian J Gangle
(74) Attorney, Agent, or Firm — Young & Thompson

(57) ABSTRACT

The invention provides a composition for the inoculation in a plant of agrobacteria transfected by expression vectors, in order to produce in said plant a protein of interest or a derivative of said protein, by deletion or by mutation, characterized in that it comprises
agrobacteria transfected by at least one expression vector, comprising a nucleotide sequence insert that codes for said protein or a derivative of said protein, and
agrobacteria transfected by a plurality of expression vectors, each comprising at least one nucleotide sequence insert that codes for proteins having a silencing suppressor effect.

10 Claims, 5 Drawing Sheets

Figure 1:
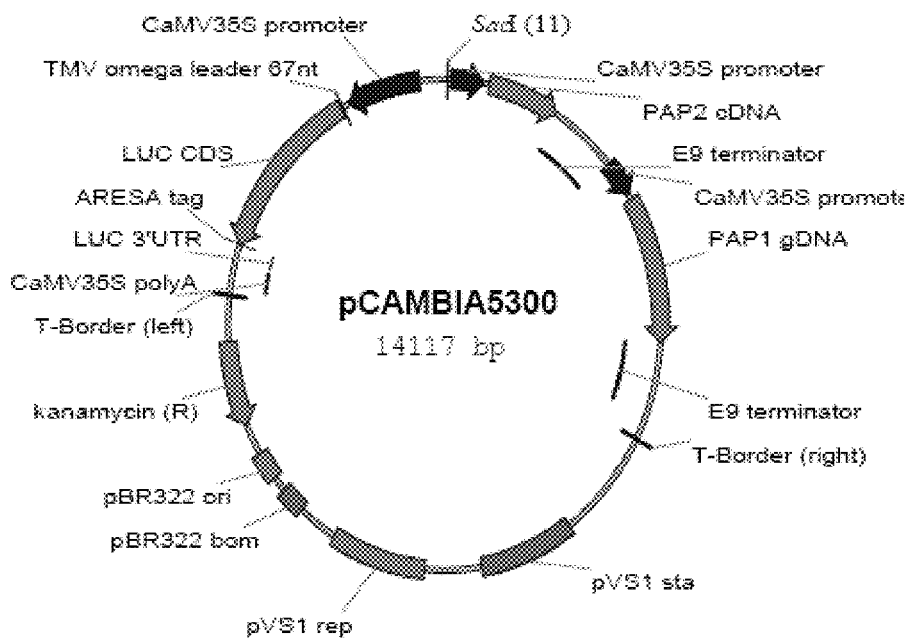

1_ Mock
2_ P1-A20T
3_ P1-K54G
4_ P1-Q66R
5_ P1 Tz3
6_ P1 IYMV
7_ Ladder
8_ Ladder Not reduced 20 µg/well Anti Ldi IJ11 sense 1/2000

T+ = 25 µl of Leishmania supernatant

Mock = ½ empty A4K7 + ½ cocktail with Tz3 P1

Cocktail with IYMV P1

Not reduced
30 µg/well
Anti Ldi IJ11 sense 1/2000
T+ = 25 µl of Leishmania supernatant

PSA

1_ T+     5_ J+6
2_ Ladder   6_ J+5
3_ J+8     7_ J+3
4_ J+7     8_ Mock

Mock = ½ empty A4K7 + ½ cocktail with Tz3 P1

Figure 7

Quantity used in ng/Western on PSA A3B with rabbit anti-C-ter 1   3   5   7   10   15   20   30   40   50

P1-A20T
P1-K54G
P1 Tz3
P1 IYMV
P1-Q66R

| | Grams of fresh material | Grams of powder recovered | Quantity extracted in 200 µl of buffer | Quantity used per 20 µg of total proteins | Quantity detected (see range) | YIELDS per 100 g of powder | |
|---|---|---|---|---|---|---|---|
| P1 20 | 11.5 g | 11.18 | 0.16 | 4.57 µl | 10 à 15 ng | 243 µg | 364 µg |
| P1 54 | 13.3 g | 12.14 | 0.14 | 3.81 µl | 10 à 15 ng | 374 µg | 562 µg |
| P1 66 | 13.7 g | 15.47 | 0.15 | 4.17 µl | 30 à 40 ng | 0.852 mg | 1.27 mg |
| P1 IYMV | 1.7 g 2 J+6 | 0.92 | 0.18 | 5.02 µl | 25 ng | 345 µg | |
| P1 Tz3 | 11.3 g | 11.14 | 0.18 | 3.66 µl | 10 à 15 ng | 301 µg | 452 µg |

Figure 8

Figure 9
Cloned in A4K7 (pCAMBIA1300 modified with K7 insert) cloned with BamHI and SacI PSA sp+h- tagged at N-terminus with 6 histidines 326pb 442aa 48.6 Kda (SEQ ID NO: 20):

AATTCGAGCTCGGTACCC*ATCGTACCCCTACTCCAAAAATGTCAAAGATACAGTCTCAGAAGACCA*
*AAGGGCTATTGAGACTTTTCAACAAAGGGTAATTTCGGGAAACCTCCTCGGATTCCATTGCCCAGCTA*
*TCTGTCACTTCATCGAAAGGACAGTAGAAAAGGAAGGTGGCTCCTACAAATGCCATCATTGCGATAAA*
*GGAAAGGCTATCATTCAAGATGCCTCTGCCGACAGTGGTCCCAAAGATGGACCCCCACCCACGAGGAG*
*CATCGTGGAAAAAGAAGACGTTCCAACCACGTCTTCAAAGCAAGTGGATTGATGTGACATCTCCACTG*
*ACGTAAGGGATGACGCACAATCCCACTATCCTTCGCAAGACCCTTCCTCTATATAAGGAAGTTCATTT*
*CATTTGGAGAGGACAGCCCAAGCTT*
   *GGATCC* (BamhI)
   insert
   ATGcatcaccatcaccatcacGCGCTGTGCGTGCGTCGGCTGGTGCTGGCGGCGACCCTCGCCGCT
GTGGTGGCGCTGCTGCTGTGCACGAGCAGTGCGCCGGTGGCGCGTGCTGCTGTGAAGGATGACTTCAC
TGCTGCGCAGCGGACGAACACGCTGGCGGTGCTGGAGGCGTTTGGGCGTGCGATCCCTGAGCTTGGGA
AGCTGTGGAAGGGCGACGACTTCTGCTTTTGGGAGTCGGTCGTGTGCGATGTGACCGAAGTGTACTTG
TGGGAAATCGGTGCGACGTATACCGGCACGCTGCCGGAGATGCCTGTGGACGTCGACTACACGGCCGT
CATGGTCAAGCACCTCGACTTTTCCCAAATGGGGCTGGGGCTGAGCGGAACGCTGCCGGACAGCTGGA
GCAGGCTGCAGGGACTGACCTCACTTACGTTGTCGGGCTGCGGCGTGAGCGGTACGCTGCCCCCCTCG
TGGCGCTCGATGAAGTCTTTGGTGTCGTTGTGGATTGAGAGTTGTGAAAGTGTTACCGGCAAGCTGCC
GCCTGAGTGGAGCTCGATGAAATCGCTGAGAGATCTCCATCTGCATGGCGCGAAGGTTTCCGGCACGC
TGCCGCCTGAGTGGAGCACGATGAAATCGCTGACCCTTCTCGATCTGCAGGACACTCAGGTTACCGGC
AGTCTGCCGCCTGAGTGGAGCTCAATGAAATCCATGACCATTCTCAGTCTGAATGGCGCGAAGGTTTC
CGGCACGCTGCCACCCCAGTGGAGCTCGATGACATCGCTGAGCCTTCTCAGTCTGGAGGGTACTCAGC
TCTCCGGCACGCTACCGCCCAGTGGAGTGGGATGACATCGCTGGTCACGCTTTTTCTGCAGGGTACT
CAGGTCTCCGGCACTCTGCCGCCGCAGTGGAGATCGATGTTGAATGCCGAGTTCCTGCAGCTGGAGAA
CTGCGACCTGTCCGGCTGTTTGCCCCCCGAGTGGGCTGCGATGCCGAAGCTGCGTCATGTCGAACTTA
AGGGCAACCAGTTCGCCGGGTGTGTGCCGGACTCGTGGGCTCAGAAGGCCGGTCTCGTTGTGGAAATC
GAGGATAAGCACACGGGCAACAGCTGCATTGCTGGTGCGGACTGCGCAACGACGACCACGACCACCAC
TGAACCCACGTCCACTGCGAGCCCAACAGCCACGCCTACCTCTGCCCCCGAGACGGAGTGCGAGGTGG
ATGGGTGTGAGGTGTGCGATGGGGACTCCGCGGCGAGGTGCGCCAGGTGCCGTGAGGGCTACTTCCTG
ACGGACGAGAGGACGTGCCTGGTGTACCGCGATTGA*GAGCTC (SacI)*
  *GAATTCGGTACGCTGAAATCACCAGTCTCTCTCTACAAATCTATCTCTCTCTATTTTCTCCATAAA*
*TAATGTGTGAGTAGTTTCCCGATAAGGGAAATTAGGGTTCTTATAGGGTTTCGCTCATGTGTAAGCAT*
*ATAAGAAACCCTTAGTATGTATTTGTATTTGTAAAATACTTCTATCAATAAAATTTCTAATTCCTAAA*
*ACCAAAATCCAGTACTAAAATCCAGATCGA*TGGGGATCCTCTAGAGTCGACCTGCAGGCATGCAAGCT
TGGCACTGGCCGTCGTTTTACAAC Diagram of insert

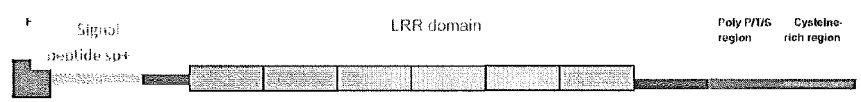

SEQUENCE LISTING

```
<160> NUMBER OF SEQ ID NOS: 20

<210> SEQ ID NO 1
<211> LENGTH: 2526
<212> TYPE: DNA
<213> ORGANISM: Leishmania amazonensis

<400> SEQUENCE: 1 gaccctgtt  gcgaatggcg  cagtgcgtgc  gtcggctggt  gctggcggcg  cccctcgccg      60
ctgtggtggc  gctgctgctg  tgcacgagca  gtgcaccggt  ggcgcgtgct  gcggggacga     120
gcgacttcac  tgaggcgcag  cagacgaaca  cgctgacggt  gctgcaggcg  tttgcgcgtg     180
cgatccctgc  gcttgggggac  acgtggacgg  gcagcgactt  ctgctcgtgg  aagcacatca    240
tctgcgactc  ccccggcgtc  ggcgtgtgga  tgggcgatgt  ggattatacc  ggcacgctgc    300
cggagatgcc  tgcgagcgtc  gactacaagg  acgtcatgat  cacggaactg  aacttcagcg    360
caatgggcca  ggggctgagc  gggacgctgc  cccctcatg   gagctcgctg  acgtccttga    420
tatcactgtg  catcgaaaag  tctgagaagg  tcaccggcac  gctgcctgcc  cagtggagct    480
cgatgacgtc  gctggacaac  cttaacctgc  acgacacggc  ggtctccggc  acgctgcctg    540
cccagtggag  ctcgatgaag  cagctgaccg  ttctggatct  ggagggcact  aaggtgtccg    600
gcacgctgcc  gtccgagtgg  agtgggatgg  cgaaggccga  ggccgtgcag  ctggagaact    660
gcggtctgtc  cgggagtctg  cccccctcgt  ggtctgcgat  gccgaagctg  cgtatcgtct    720
cactgagcgg  caaccacttc  tgcgggtgcg  tgcccgactc  gtggagggag  aaggaccgcc    780
tcgatgtgac  catcgaggaa  tggcacatgg  gcgaggactg  caagcttgct  aacgcctgcc    840
gcccgactgc  tgctccggga  acgaccacga  ctaacccgcc  caccaccacc  ggcaccccag    900
cagcctcctc  tactccttct  ccagggtcgg  ggtgcgaggt  ggatgggtgt  gaggtgtgcg    960 aggggactc   cgctgcgcgg  tgcgccaggt  gccgtgaggg  ctactccctg  acggacgaga   1020
agacgtgcct  ggcgaaccac  gatggcggcg  tggcggcggc  gtcgagcgga  gcggtggctg   1080
ccgctgctgt  gtgggcggct  gtgctgttga  gcgtgggggct  ggtggcgtga  gggtgcggcg   1140
ggcacacgcg  cacgcgcaca  cgccgtcgtg  catcgcgtgt  gctttccgcc  gttgtggcgc   1200
```

```
ctgcacggat gcacgggcat gcggaggcgt gcatgcgtgt gcgcgtgcca gctcttgtgt    1260
gtctctccgt gtggccagca gtcggcaccc gcgccgatcg aatgtgcgcg cggcggcggt    1320
gtgtcgcctt ggacagcgga tgcgggcgcc cgcccctcgc cgtgtgccct gcggtctgct    1380
gtgctgccgc gcgagcgacg tacgcgatgcg ctgtccggcc ctcttcgacg gggctcgctt    1440
```

```
gcggtgctgt gctctcgtgg tctgtgccgg tgctgccctg gcggggtgag agctggcggg    1500
ggcgtgggtg cgcgcgcggc agctctccgc tgcgttgagg gcggcctgcc cctgcgtccg    1560
cgcaccgtcg cgctctcctc gacgccactg cgcgcgcttg ttggcttgct ttgctctgtc    1620
gtgcgcactc tctcttattt tccgtttcat tcgcctgtat tctcttctcc caccgcactg    1680
cggcctcgtc accgcggccg tgcggtgcgc aggcgggtga tgtgccgttg tgccccccct    1740 ttcatgcgc gctgggccga tcgccctctt gcctccctcc tcccctccc cctcccgccg     1800 gtcctgtcaa ttgtatatcc gtggacctta tcttcgtact gcctccgcgc ctcttccgta    1860
aagcttcgtt ggcgtgtgcc gccccccgga cgtcagcgcc gctgtgctcg catgctcacg    1920
gtgcgtcccc gtgcgtgggc gtgcacgtaa ggacatgtat atatgtatgt gtatgtatat    1980
gagtatgtat atatgtacgg ttatatatag gaatttgtgt atgttgaggt gtatgcatgt    2040
gcgtgcgtat attagtgtgt gcgagcacgc gtgttgcgcc acgctctgct gcccgcctcc    2100
gctgtgcgtg tcactcgctg tgggcgcggt ggcgggtggc gccgggtggt ggccgtgcgg    2160
cgggcggggg ctcctctgtg tttctctatt tctctgttcc ctgttgacct caaaaaaaaa    2220
aaaaaaaaaa aaagtgcacg taaggacatg tatatatgta tgtgtatgta tatgagtatg    2280
tatatatgta cggttatata taggaatttg tgtatgttga ggtgtatgca tgtgcgtgcg    2340
tatattagtg tgtgcgagca cgcgtgttgc gccacgctct gctgcccgcc tccgctgtgc    2400
gtgtcactcg ctgtgggcgc ggtggcgggt ggcgccgggt ggtggccgtg cggcgggcgg    2460
gggctcctct gtgtttctct atttctctgt tccctgttga cctcaaaaaa aaaaaaaaaa    2520
aaaaaa                                                               2526
```

<210> SEQ ID NO 2
<211> LENGTH: 1401
<212> TYPE: DNA
<213> ORGANISM: Leishmania amazonensis

<400> SEQUENCE: 2

```
cgtggacggg cagcgacttc tgctcgtgga agcacatcat ctgcgactcc cccggcgtcg      60
gcgtgtggat gggcgatgtg gattataccg gcacgctgcc ggagatgcct gcgagcgtcg     120
actacaagga cgtcatgatc acggaactga acttcagcgc aatgggccag gggctgagcg     180
ggacgctgcc cccctcatgg agctcgctga cgtccttgat atcactgtgc atcgaaaagt     240
ctgagaaggt caccggcacg ctgcctgccc agtggagctc gatgacgtcg ctggacaacc     300
ttaacctgca cgacacggcg gtctccggca cgctgcctgc ccagtggagc tcgatgaagc     360
agctgaccgt tctggatctg gagggcacta aggtgtccgg cacgctgccg tccgagtgga     420
gtgggatggc gaaggccgag gccgtgcagc tggagaactg cggtctgtcc gggagtctgc     480 cccccctcgtg gtctgcgatg ccgaagctgc gtatcgtctc actgagcggc aaccacttct     540
gcgggtgcgt gcccgactcg tggagggaga aggaccgcct cgatgtgacc atcgaggaat     600
ggcacatggg cgaggactgc aagcttgcta acgcctgccg cccgactgct gctcggcgaa     660
cgaccacgac taacccgccc accaccaccg gcaccccagc agcctcctct actccttctc     720
```

-continued

```
cagggtcggg gtgcgaggtg gatgggtgtg aggtgtgcga gggggactcc gctgcgcggt    780
gcgccaggtg ccgtgagggc tactccctga cggacgagaa gacgtgcgtg gcgaaccacg    840
atggcggcgt ggcggcggcg tcgagcggag cggtggctgc cgctgctgtg tgggcggctg    900
tgctgttgag cgtggggctg gtggcgtgag ggtgcggcgg gccccctcttc tctgtggtgc    960
ccctggtgcc tgccctcgcc cccggcacgg cgtcgtcgct gccctctctc accccacca    1020
gccgacgggg agaccgacag ccacacgcgc acgcgcacac gccgtcgtgc atcgcgtgtg    1080
cgtgcactta aggacatgta tatatgtatg tgtatgtata tgagtatgta tatatgtccg    1140
gttatatata ggaatttgtg tatgttgagg tgtatgcatg tgcgtgcgta tattagtctg    1200
tgcgagcacg cgtgttgcgc cacgctttgc tgcccgcctc cgctgtgcgt gtccctccct    1260
gtgggcgcgc tgccgggtgg ccccgggtgg tgcccgtgcg gcgggcgggg gctcctctgt    1320
gtttctctat ttctctgttc cctgttgacc ccaaaaaaaa aaaaaaaaaa aaaaaaaaa    1380
aaaaaaaaaa aaaaaaaaaa a                                              1401
```

<210> SEQ ID NO 3
<211> LENGTH: 1684
<212> TYPE: DNA
<213> ORGANISM: Leishmania amazonensis

<400> SEQUENCE: 3

```
ggacgggcag cgacttctgc tcgtggaagc acatcatctg cgactccccc ggcgtcggcg     60
tgtggatggg cgatgtggat tataccggca cgctgccgga gatgcctgcg agcgtcgact    120
acaaggacgt catgatcatg gcactggact tcggcgcaat gggccaggga ctgagcggga    180
cgctgccccc ctcatggagc tcgctgacgt ccttgatgtc actgtggatc gaaaagtctg    240
agaaggtcac cggcacgctg cctacccagt ggagctcgat gaagcagctg acccttctgc    300
atctgaaggg cactaaggtg tccggcacgc tgccgcccga gtggagtggg atgacgtcgc    360
tggacgacct taacctgcac gacacggcgg tctccggcac gctgcctgcc cagtggagct    420
cgatgaagca gctgatcgat ctggatctgg agggcactaa ggtgtccggc acgctgccgc    480
ccgagtggag tgggatggcg aaggccgagg ccctgcagct gaagtactgc gatctgtccg    540
ggagtctgcc cccctcgtgg tcttcgatgc agaagctgcg tatcgtctca ctgagcggca    600
accacttctg cgggtgcgtg cccgactcgt ggagggagaa ggaccgcctc gatgtgacca    660
tcgaggaatg gcacatgggc gaggactgca agcttgctaa cgcctgccgc ccgactgctg    720
ctccgggaac gaccacgact aacccgccca ccaccaccgg caccccagca gcctcctcta    780
ctccttctcc agggtcgggg tgcgaggtgg atgggtgtga ggtgtgcgag ggggactccg    840
ctgcgcggtg cgccaggtgc cgtgagggct actccctgac ggacgagaag acgtgcctgg    900
cgaaccacga tggcggcgtg gcggcggcgt cgagcggagc ggtggctgcg gctgctgtgt    960
gggcggctgt gctgttgagc gtggggctgg tggcgtgagg gtgcggcggc ccctcttct    1020
ctgtggtgcc cctggtgcct gccctcgccc cagcacggc gtcgtcgctg ccctctcacc    1080
cccaccagcc gaagggggaga ccgacagcca cacgcacacg cgcacgcgcc gtcgtgcatc    1140
gcgtgtgctt ccgccgttg tggcgcctgc gcggatgcac gggcatgcgg aggcgtgcat    1200
gcgtgtgcgc gtgccagctc ttgtgtgtct tccgtgtgg ccagcagtcg gcacccgcgc    1260
cgatcgaatg tgcgcgcggc gggcgtgtgt cgccttggac agcggatgcg gcgcccgccc    1320
ctcgccgtgt gccctgcggt ctgctgtgct gccgcgcgag cgacgtacgg agtgcatgta    1380
aggacatgta tatatgtatg tgtaggtata tgagtatgta tatatgtacg gttatatata    1440
```

-continued

```
ggaatttgtg tatgttgagg tgtatgcatg tgcgtgcgta tattagtctg tgcgagcacg      1500
cgtgttgcgc cacgctttgc tgcccgcctc tgctgtgcgt gtcactccct gtgggcgcgc      1560
tggcgggtgg cgccgggtgg tggccgtgcg gcgggcgggg gctcctctgt gtttctctat      1620
ttctctgttc cctgttgacc tcaagaaaaa aaaaaaaaaa aaaaaaaaaa aaaaaaaaaa      1680
aaaa                                                                   1684
```

<210> SEQ ID NO 4
<211> LENGTH: 1404
<212> TYPE: DNA
<213> ORGANISM: Leishmania amazonensis

<400> SEQUENCE: 4

```
tcggcgtgtg gatgggcgat gtggattata ccggcacgct gccggagatg cctgcgagcg       60
tcgactacaa ggacgtcatg atcacggaac tgaacttcgg cgcaatgggc cagggactga      120
gcgggacgct gccccccctca tggagctcga tgaagcagct gatcgatctg gatctggagg      180
gcactaaggt gtccggcacg ctgccgcccg agtggagtgg gatggcgaag gccgaggccc      240
tgcagctgaa gtactgcgat ctgtccggga gtctgccccc ctcgtggtct tcgatgcaga      300
agctgcgtat cgtctcactg agcggcaacc acttctgcgg gtgcgtgccc gactcgtgga      360
gggagaagga ccgcctcgat gtgaccatcg aggaatggca catgggcgag gactgcaagc      420
ttgctaacgc ctgccgcccg actgctgctc cgggaacgac cacgactaac ccgcccacca      480
ccaccggcac cccagcagcc tcctctactc cttctccagg gtcggggtgc gaggtggatg      540
ggtgtgaggt gtgcgagggg gactccgctg cgcggtgcgc caggtgccgt gagggctact      600
ccctgacgga cgagaagacg tgcctggcga accacgatgg cggcgtggcg gcggcgtcaa      660
gcggagcggt ggctgcggct gctgtgtggg cggctgtgct gttgagcgtg gggctggtgg      720
cgtgagggtg cggcgggccc ctcttctctg tggtgcccct ggtgcctgcc ctcgcccccg      780
gcacggcgtc gtcgctgccc tctctcaccc ccaccagccg acggggagac cgacagccac      840
acgcgcacgc gcacacgccg tcgtgcatcg cgtgtgcttt ccgccgttgt ggcgcctgca      900
cggatgcacg ggcatgcgga ggcgtgcatg cgtgtgcgcg tgccagctct tgtgtgtctc      960
tccgtgtggc cagcagtcgg cacccgcgcc gatcgaatgt gcgcgcggcg gcggtgtgtc     1020
gccttggaca gcgcgatgctg gcgcccgccc ctcgcgtgtg cctcggtctg cgtgtcgtgg     1080
ccgcgcgagc gacgtacgga gtgcgctgtg tgcacttaag gacatgtata tatgtatgtg     1140
tatgtatatg agtatgtata tatgtacggt tatatatagg aatttgtgta tgttgaggtg     1200
tatgcatgtg cgtgcgtata ttagtctgtg cgagcacgcg tgttgcgcca cgctttgctg     1260
cccgcctccg ctgtgggtgt cactcgctgt gggcccggtg gcgggtggcc ccgggtggtg     1320
cccgttcggc gggcggggc tcctctgtgt ttctctattt ctctgttccc tgttgccctc     1380
caaaaaaaaa aaaaaaaaaa aaaa                                            1404
```

<210> SEQ ID NO 5
<211> LENGTH: 1501
<212> TYPE: DNA
<213> ORGANISM: Leishmania amazonensis

<400> SEQUENCE: 5

```
ccggcgtcgg cgtgtggatg ggcgatgtgg attataccgg cacgctgccg gagatgcctg       60
cgagcgtcga ctacaaggac gtcatgatca cggaactgaa cttcagcgca atgggccagg      120
```

-continued

```
ggctgagcgg gacgctgccc ccctcatgga gctcgctgac gtccttgata tcactgtgca    180
tcgaaaagtc tgagaaggtc accggcacgc tgcctgccca gtggagctcg atgacgtcgc    240
tggacaacct taacctgcac gacacggcgg tctccggcac gctgccgccc gagtggagtg    300
ggatgacgtc gctggacgac cttaacctgc acgacacggc ggtctccggc acgctgcctg    360
cccagtggag ctcgatgaag cagctgatcg atctggatct ggagggcact aaggtgtccg    420
gcacgctgcc gcccgagtgg agtgggatgg cgaaggccga ggccctgcag ctgaagtact    480
gcgatctgtc cggagtctg cccccctcgt ggtcttcgat gcagaagctg cgtatcgtct    540
cactgagcgg caaccacttc tgcgggtgcg tgcccgactc gtggagggag aaggaccgcc    600
tcgatgtgac catcgaggaa tggcacatgg gcgaggactg caagcttgct aacgcctgcc    660
gcccgactgc tgctccggga acgaccacga ctaacccgcc caccaccacc ggcaccccag    720
cagcctcctc tactccttct ccagggtcgg ggtgcgaggg ggatgggtgt gaggtgtgcg    780
aggggggactc cgctgcgcgg tgcgccaggt gccgtgaggg ctactccctg acggacgaga    840
agacgtgcct ggcgaaccac gatggcggcg tggcggcggg gtcaagcgga gcggtggctg    900
cggctgctgt gtgggcggct gtgctgttga gcgtggggct ggtggcgtga gggtgccgcc    960
gcccctctt ctctgtggtg ccctggtgc ctgcctcgc cccagcacg gggtcgtcgc       1020
tgccctctca ccccaccag ccgaagggga gaccgacagc cacacgcaca cgcgcacgcg    1080
ccgtcgtgca tcgcgtgtgc tttccgccgt tgtggcgcct cgcggatgc acgggcatgc    1140
ggaggcgtgc atgcgtgtgc gcgtgccaac tcttgtgtgt ctctccgtgt ggccagcagt    1200
cggcacccgt gcacgtaagg acatgtatat atgtatgtgt aggtatatga gtatgtatat    1260
atgtacggtt atatatagga atttgtgtat gttgaggtgt atgcatgtgc gtgcgtatat    1320
tagtctgtgc gagcacgcgt gttgcgccac gctctgctgc ccgcctctgc tgtgcgtgtc    1380
actcgctgtg ggcgcgctgg cgggtggcgc cgggtggtgg ccgtgcggcg ggcggggct    1440
cctctgtgtt tctctatttc tctgttccct gttgacctca agaaaaaaaa aaaaaaaaaa    1500
a                                                                    1501
```

<210> SEQ ID NO 6
<211> LENGTH: 371
<212> TYPE: PRT
<213> ORGANISM: Leishmania amazonensis

<400> SEQUENCE: 6

```
Met Ala Gln Cys Val Arg Arg Leu Val Leu Ala Ala Pro Leu Ala Ala
1               5                   10                  15

Val Val Ala Leu Leu Cys Thr Ser Ser Ala Pro Val Ala Arg Ala
                20                  25                  30

Ala Gly Thr Ser Asp Phe Thr Glu Ala Gln Gln Thr Asn Thr Leu Thr
            35                  40                  45

Val Leu Gln Ala Phe Ala Arg Ala Ile Pro Ala Leu Gly Asp Thr Trp
        50                  55                  60

Thr Gly Ser Asp Phe Cys Ser Trp Lys His Ile Ile Cys Asp Ser Pro
65                  70                  75                  80

Gly Val Gly Val Trp Met Gly Asp Val Asp Tyr Thr Gly Thr Leu Pro
                85                  90                  95

Glu Met Pro Ala Ser Val Asp Tyr Lys Asp Val Met Ile Thr Glu Leu
                100                 105                 110

Asn Phe Ser Ala Met Gly Gln Gly Leu Ser Gly Thr Leu Pro Pro Ser
            115                 120                 125
```

```
Trp Ser Ser Leu Thr Ser Leu Ile Ser Leu Cys Ile Glu Lys Ser Glu
        130                 135                 140

Lys Val Thr Gly Thr Leu Pro Ala Gln Trp Ser Ser Met Thr Ser Leu
145                 150                 155                 160

Asp Asn Leu Asn Leu His Asp Thr Ala Val Ser Gly Thr Leu Pro Ala
                165                 170                 175

Gln Trp Ser Ser Met Lys Gln Leu Thr Val Leu Asp Leu Glu Gly Thr
                180                 185                 190

Lys Val Ser Gly Thr Leu Pro Ser Glu Trp Ser Gly Met Ala Lys Ala
            195                 200                 205

Glu Ala Val Gln Leu Glu Asn Cys Gly Leu Ser Gly Ser Leu Pro Pro
    210                 215                 220

Ser Trp Ser Ala Met Pro Lys Leu Arg Ile Val Ser Leu Ser Gly Asn
225                 230                 235                 240

His Phe Cys Gly Cys Val Pro Asp Ser Trp Arg Glu Lys Asp Arg Leu
                245                 250                 255

Asp Val Thr Ile Glu Glu Trp His Met Gly Glu Asp Cys Lys Leu Ala
                260                 265                 270

Asn Ala Cys Arg Pro Thr Ala Ala Pro Gly Thr Thr Thr Thr Asn Pro
            275                 280                 285

Pro Thr Thr Thr Gly Thr Pro Ala Ala Ser Ser Thr Pro Ser Pro Gly
    290                 295                 300

Ser Gly Cys Glu Val Asp Gly Cys Glu Val Cys Glu Gly Asp Ser Ala
305                 310                 315                 320

Ala Arg Cys Ala Arg Cys Arg Glu Gly Tyr Ser Leu Thr Asp Glu Lys
                325                 330                 335

Thr Cys Leu Ala Asn His Asp Gly Gly Val Ala Ala Ser Ser Gly
                340                 345                 350

Ala Val Ala Ala Ala Val Trp Ala Ala Val Leu Leu Ser Val Gly
            355                 360                 365

Leu Val Ala
    370

<210> SEQ ID NO 7
<211> LENGTH: 286
<212> TYPE: PRT
<213> ORGANISM: Leishmania amazonensis

<400> SEQUENCE: 7

Met Gly Asp Val Asp Tyr Thr Gly Thr Leu Pro Glu Met Pro Ala Ser
1               5                   10                  15

Val Asp Tyr Lys Asp Val Met Ile Thr Glu Leu Asn Phe Ser Ala Met
            20                  25                  30

Gly Gln Gly Leu Ser Gly Thr Leu Pro Pro Ser Trp Ser Ser Leu Thr
        35                  40                  45

Ser Leu Ile Ser Leu Cys Ile Glu Lys Ser Glu Lys Val Thr Gly Thr
    50                  55                  60

Leu Pro Ala Gln Trp Ser Ser Met Thr Ser Leu Asp Asn Leu Asn Leu
65                  70                  75                  80

His Asp Thr Ala Val Ser Gly Thr Leu Pro Ala Gln Trp Ser Ser Met
                85                  90                  95

Lys Gln Leu Thr Val Leu Asp Leu Glu Gly Thr Lys Val Ser Gly Thr
            100                 105                 110

Leu Pro Ser Glu Trp Ser Gly Met Ala Lys Ala Glu Ala Val Gln Leu
```

```
            115                 120                 125

Glu Asn Cys Gly Leu Ser Gly Ser Leu Pro Ser Trp Ser Ala Met
    130                 135                 140

Pro Lys Leu Arg Ile Val Ser Leu Ser Gly Asn His Phe Cys Gly Cys
145                 150                 155                 160

Val Pro Asp Ser Trp Arg Glu Lys Asp Arg Leu Asp Val Thr Ile Glu
                165                 170                 175

Glu Trp His Met Gly Glu Asp Cys Lys Leu Ala Asn Ala Cys Arg Pro
            180                 185                 190

Thr Ala Ala Pro Gly Thr Thr Thr Asn Pro Pro Thr Thr Gly
            195                 200                 205

Thr Pro Ala Ala Ser Ser Thr Pro Ser Pro Gly Ser Gly Cys Glu Val
        210                 215                 220

Asp Gly Cys Glu Val Cys Glu Gly Asp Ser Ala Ala Arg Cys Ala Arg
225                 230                 235                 240

Cys Arg Glu Gly Tyr Ser Leu Thr Asp Glu Lys Thr Cys Val Ala Asn
                245                 250                 255

His Asp Gly Gly Val Ala Ala Ala Ser Ser Gly Ala Val Ala Ala Ala
            260                 265                 270

Ala Val Trp Ala Ala Val Leu Leu Ser Val Gly Leu Val Ala
        275                 280                 285

<210> SEQ ID NO 8
<211> LENGTH: 310
<212> TYPE: PRT
<213> ORGANISM: Leishmania amazonensis

<400> SEQUENCE: 8

Met Gly Asp Val Asp Tyr Thr Gly Thr Leu Pro Glu Met Pro Ala Ser
1               5                   10                  15

Val Asp Tyr Lys Asp Val Met Ile Met Ala Leu Asp Phe Gly Ala Met
                20                  25                  30

Gly Gln Gly Leu Ser Gly Thr Leu Pro Pro Ser Trp Ser Ser Leu Thr
            35                  40                  45

Ser Leu Met Ser Leu Trp Ile Glu Lys Ser Glu Lys Val Thr Gly Thr
    50                  55                  60

Leu Pro Thr Gln Trp Ser Ser Met Lys Gln Leu Thr Leu His Leu
65                  70                  75                  80

Lys Gly Thr Lys Val Ser Gly Thr Leu Pro Pro Glu Trp Ser Gly Met
                85                  90                  95

Thr Ser Leu Asp Asp Leu Asn Leu His Asp Thr Ala Val Ser Gly Thr
            100                 105                 110

Leu Pro Ala Gln Trp Ser Ser Met Lys Gln Leu Ile Asp Leu Asp Leu
        115                 120                 125

Glu Gly Thr Lys Val Ser Gly Thr Leu Pro Pro Glu Trp Ser Gly Met
    130                 135                 140

Ala Lys Ala Glu Ala Leu Gln Leu Lys Tyr Cys Asp Leu Ser Gly Ser
145                 150                 155                 160

Leu Pro Pro Ser Trp Ser Ser Met Gln Lys Leu Arg Ile Val Ser Leu
                165                 170                 175

Ser Gly Asn His Phe Cys Gly Cys Val Pro Asp Ser Trp Arg Glu Lys
            180                 185                 190

Asp Arg Leu Asp Val Thr Ile Glu Glu Trp His Met Gly Glu Asp Cys
        195                 200                 205
```

```
Lys Leu Ala Asn Ala Cys Arg Pro Thr Ala Ala Pro Gly Thr Thr Thr
210                 215                 220

Thr Asn Pro Pro Thr Thr Thr Gly Thr Pro Ala Ala Ser Ser Thr Pro
225                 230                 235                 240

Ser Pro Gly Ser Gly Cys Glu Val Asp Gly Cys Glu Val Cys Glu Gly
                245                 250                 255

Asp Ser Ala Ala Arg Cys Ala Arg Cys Arg Glu Gly Tyr Ser Leu Thr
                260                 265                 270

Asp Glu Lys Thr Cys Leu Ala Asn His Asp Gly Val Ala Ala Ala
                275                 280                 285

Ser Ser Gly Ala Val Ala Ala Ala Val Trp Ala Ala Val Leu Leu
290                 295                 300

Ser Val Gly Leu Val Ala
305                 310

<210> SEQ ID NO 9
<211> LENGTH: 307
<212> TYPE: PRT
<213> ORGANISM: Leishmania amazonensis

<400> SEQUENCE: 9

Met Cys Val Arg Ile Leu Val Cys Ala Ser Thr Arg Val Ala Pro Arg
1               5                   10                  15

Phe Ala Arg Leu Arg Cys Gly Cys His Ser Leu Trp Ala Arg Trp
                20                  25                  30

Arg Val Ala Pro Gly Gly Ala Arg Ser Ala Gly Gly Ser Ser Val
                35                  40                  45

Phe Leu Tyr Phe Ser Val Pro Cys Cys Pro Lys Lys Lys Lys
50                  55                  60

Lys Lys Ile Gly Val Trp Met Gly Asp Val Asp Tyr Thr Gly Thr Leu
65                  70                  75                  80

Pro Glu Met Pro Ala Ser Val Asp Tyr Lys Asp Val Met Ile Thr Glu
                85                  90                  95

Leu Asn Phe Gly Ala Met Gly Gln Gly Leu Ser Gly Thr Leu Pro Pro
                100                 105                 110

Ser Trp Ser Ser Met Lys Gln Leu Ile Asp Leu Asp Leu Glu Gly Thr
                115                 120                 125

Lys Val Ser Gly Thr Leu Pro Pro Glu Trp Ser Gly Met Ala Lys Ala
                130                 135                 140

Glu Ala Leu Gln Leu Lys Tyr Cys Asp Leu Ser Gly Ser Leu Pro Pro
145                 150                 155                 160

Ser Trp Ser Ser Met Gln Lys Leu Arg Ile Val Ser Leu Ser Gly Asn
                165                 170                 175

His Phe Cys Gly Cys Val Pro Asp Ser Trp Arg Glu Lys Asp Arg Leu
                180                 185                 190

Asp Val Thr Ile Glu Glu Trp His Met Gly Glu Asp Cys Lys Leu Ala
                195                 200                 205

Asn Ala Cys Arg Pro Thr Ala Ala Pro Gly Thr Thr Thr Asn Pro
210                 215                 220

Pro Thr Thr Thr Gly Thr Pro Ala Ala Ser Ser Thr Pro Ser Pro Gly
225                 230                 235                 240

Ser Gly Cys Glu Val Asp Gly Cys Glu Val Cys Glu Gly Asp Ser Ala
                245                 250                 255

Ala Arg Cys Ala Arg Cys Arg Glu Gly Tyr Ser Leu Thr Asp Glu Lys
                260                 265                 270
```

```
Thr Cys Leu Ala Asn His Asp Gly Gly Val Ala Ala Ser Ser Gly
        275                 280                 285

Ala Val Ala Ala Ala Val Trp Ala Ala Val Leu Leu Ser Val Gly
290                 295                 300

Leu Val Ala
305

<210> SEQ ID NO 10
<211> LENGTH: 310
<212> TYPE: PRT
<213> ORGANISM: Leishmania amazonensis

<400> SEQUENCE: 10

Met Gly Asp Val Asp Tyr Thr Gly Thr Leu Pro Glu Met Pro Ala Ser
1               5                   10                  15

Val Asp Tyr Lys Asp Val Met Ile Thr Glu Leu Asn Phe Ser Ala Met
                20                  25                  30

Gly Gln Gly Leu Ser Gly Thr Leu Pro Pro Ser Trp Ser Ser Leu Thr
            35                  40                  45

Ser Leu Ile Ser Leu Cys Ile Glu Lys Ser Glu Lys Val Thr Gly Thr
50                  55                  60

Leu Pro Ala Gln Trp Ser Ser Met Thr Ser Leu Asp Asn Leu Asn Leu
65                  70                  75                  80

His Asp Thr Ala Val Ser Gly Thr Leu Pro Pro Glu Trp Ser Gly Met
                85                  90                  95

Thr Ser Leu Asp Asp Leu Asn Leu His Asp Thr Ala Val Ser Gly Thr
            100                 105                 110

Leu Pro Ala Gln Trp Ser Ser Met Lys Gln Leu Ile Asp Leu Asp Leu
        115                 120                 125

Glu Gly Thr Lys Val Ser Gly Thr Leu Pro Pro Glu Trp Ser Gly Met
130                 135                 140

Ala Lys Ala Glu Ala Leu Gln Leu Lys Tyr Cys Asp Leu Ser Gly Ser
145                 150                 155                 160

Leu Pro Pro Ser Trp Ser Ser Met Gln Lys Leu Arg Ile Val Ser Leu
                165                 170                 175

Ser Gly Asn His Phe Cys Gly Cys Val Pro Asp Ser Trp Arg Glu Lys
            180                 185                 190

Asp Arg Leu Asp Val Thr Ile Glu Glu Trp His Met Gly Glu Asp Cys
        195                 200                 205

Lys Leu Ala Asn Ala Cys Arg Pro Thr Ala Ala Pro Gly Thr Thr Thr
210                 215                 220

Thr Asn Pro Pro Thr Thr Thr Gly Thr Pro Ala Ala Ser Ser Thr Pro
225                 230                 235                 240

Ser Pro Gly Ser Gly Cys Glu Val Asp Gly Cys Glu Val Cys Glu Gly
                245                 250                 255

Asp Ser Ala Ala Arg Cys Ala Arg Cys Arg Glu Gly Tyr Ser Leu Thr
            260                 265                 270

Asp Glu Lys Thr Cys Leu Ala Asn His Asp Gly Gly Val Ala Ala Ala
        275                 280                 285

Ser Ser Gly Ala Val Ala Ala Ala Val Trp Ala Ala Val Leu Leu
290                 295                 300

Ser Val Gly Leu Val Ala
305                 310
```

<210> SEQ ID NO 11
<211> LENGTH: 3088
<212> TYPE: DNA
<213> ORGANISM: Leishmania infantum

<400> SEQUENCE: 11

| | | | | | |
|---|---|---|---|---|---|
| gcgctgctgc | cgctggcgct | gttgtgtgtg | tgctggggcc | gcgccacgca | cacgcacggt | 60 |
| agtgagggggg | agccgcagcg | accgaccggg | cggagcgggc | gggcggaggg | gggcgctccc | 120 |
| gcccgctggt | catgctctct | gtttcgctgg | ccggcctctc | tacgccgctg | gcgtgggcgg | 180 |
| agctccgcgc | tgcgtatcgc | tcgcccctcg | ctgcccctcc | ctgcccctcc | tcatgtgcac | 240 |
| tgctccctcc | ctctccctcc | ctctacactc | ctcgctgtcc | cctcggccga | cctccacgga | 300 |
| cacgcagacg | tgcgtgcgca | tacacaccac | ccctcacctc | gctgctgctg | ctgtgacagc | 360 |
| tctacggacc | ctgcccagtc | gctgcgcccc | cgccacccgc | ctctgtcccc | cgcacgaggg | 420 |
| tacctacgac | gtgccggcca | ccccgctctg | cccgataagc | tgagctggcg | ctcacgcccg | 480 |
| agcaatcccc | tcacggatct | gctgccgcgc | cgcactgctc | ttgaccctgg | ctgcgaatgg | 540 |
| cgctgtgcgt | gcgtcggctg | gtgctggcgg | cgaccctcgc | cgctgtggtg | gcgctgctgc | 600 |
| tgtgcacgag | cagtgcgccg | gtggcgcgtg | ctgctgtgaa | ggatgacttc | actgctgcgc | 660 |
| agcggacgaa | cacgctggcg | gtgctggagg | cgtttgggcg | tgcgatccct | gagcttggga | 720 |
| agctgtggaa | gggcgacgac | ttctgctttt | gggagtcggt | cgtgtgcgat | gtgaccgaag | 780 |
| tgtacttgtg | ggaaatcggt | gcgacgtata | ccggcacgct | gccggagatg | cctgtggacg | 840 |
| tcgactacac | ggccgtcatg | gtcaagcacc | tcgactttc | ccaaatgggg | ctggggctga | 900 |
| gcggaacgct | gccggacagc | tggagcaggc | tgcagggact | gacctcactt | acgttgtcgg | 960 |
| gctgcgcgt | gagcggtacg | ctgccccct | cgtggcgctc | gatgaagtct | ttggtgtcgt | 1020 |
| tgtggattga | gagttgtgaa | agtgttaccg | gcaagctgcc | gcctgagtgg | agctcgatga | 1080 |
| aatcgctgag | agatctccat | ctgcatggcg | cgaaggtttc | cggcacgctg | ccgcctgagt | 1140 |
| ggagcacgat | gaaatcgctg | acccttctcg | atctgcagga | cactcaggtt | accggcagtc | 1200 |
| tgccgcctga | gtggagctca | atgaaatcca | tgaccattct | cagtctgaat | ggcgcgaagg | 1260 |
| tttccggcac | gctgccaccc | cagtggagct | cgatgacatc | gctgagcctt | ctcagtctgg | 1320 |
| agggtactca | gctctccggc | acgctaccgc | cccagtggag | tgggatgaca | tcgctggtca | 1380 |
| cgcttttct | gcagggtact | caggtctccg | gcactctgcc | gccgcagtgg | agatcgatgt | 1440 |
| tgaatgccga | gttcctgcag | ctggagaact | gcgacctgtc | cggctgtttg | cccccgagt | 1500 |
| gggctgcgat | gccgaagctg | cgtcatgtcg | aacttaaggg | caaccagttc | gccgggtgtg | 1560 |
| tgccggactc | gtgggctcag | aaggccggtc | tcgttgtgga | aatcgaggat | aagcacacgg | 1620 |
| gcaacagctg | cattgctggt | gcggactgcg | caacgacgac | cacgaccacc | actgaaccca | 1680 |
| cgtccactgc | gagcccaaca | gccacgccta | cctctgcccc | cgagacggag | tgcgaggtgg | 1740 |
| atgggtgtga | ggtgtgcgat | ggggactccg | cggcgaggtg | cgccaggtgc | cgtgagggct | 1800 |
| acttcctgac | ggacgagagg | acgtgcctgg | tgtaccgcga | tggcggcgtt | gtggccgtgt | 1860 |
| cgatcggagc | ggctgctgcc | gctgttgtgt | gcatggctgt | gctgctgagc | gtggggctgg | 1920 |
| cggcgtgagg | atgccgctgc | tgtcgcgcgc | aggcggcggc | acccgctgcg | tggcacacga | 1980 |
| ctgcgtgctt | gcgtgcagca | ccgcgccctg | cattggcgtg | cgtgtgcgcg | tctgtgtgtg | 2040 |
| catggctgct | gacggtgcct | tcgtcctgcc | ctctcgctgc | ctctgcctct | ctccgcgtgt | 2100 |
| gaatgctgtg | ggctgtgttt | ggggctctcg | tgcggcgctg | ctgtacggct | gctgcttctt | 2160 |

```
ctccaccctc tctctcgca tgccggcgag ggaggggtgg cacgtgcgcg tgtgccgctg    2220
cgcttgcgag tgcgtctgtg tgtgggcctt caccacgtgc tacggtcacg ccttctcggc    2280
tggccactcg cggcgctgag ggcggtgtgc ccttcccctc gagcgccgtc gcactctctt    2340
ccgcgcgcct gcgcgggctt cttcgtgcgc tgtgctcagc cgtgcgctct cacctctttc    2400
ccttttcatt cgcttgtctt ctctcttctc ccccgcact gcggtctccc ctcctctgcc    2460
gtgcggtgcg caggcgggtg acttgccgtt gcgtctcccc ctttcgtgga gcgctgagcc    2520
gatcccctt cggcctccct cctccctcct cccgtgggtc ctgtctgttg tacatcgtcg    2580
gaccgtctct tcgtgttgcc ctccgcacc ttccgcaaat ctgcgctcgc ctgtgccgcc    2640
tctcggactt tatccttact gtgattgtat tctcacggtg cgtctccgtg tgtgtgtgtg    2700
ccacgcaccg cttcttccat gtgtgtcctt gcttgctctc gtctgccccc ccccctctgc    2760
ctcacacatt ccgtgcgtgt gtgcatcacc gttgggcggc gacatcggtg cccgtccctg    2820
ccaccctcta ctccctcatt ctcttgccac ttcgtgggcg gtgcgtgcat gcatggatgt    2880
atatacacgc atagagggt ggggacgcgg gggatcctct agagtcgacc tgcaggcatg    2940
caagcttggc gtaatcatgg tcatagctgt ttcctgtgtg aaattgttat ccgctcacaa    3000
ttccacacaa catacgagcc ggaagcataa agtgtaaagc ctggggtgcc taatgagtga    3060
gctaactcac attaattgcg ttgcgctc                                       3088
```

<210> SEQ ID NO 12
<211> LENGTH: 464
<212> TYPE: PRT
<213> ORGANISM: Leishmania infantum

<400> SEQUENCE: 12

```
Met Ala Leu Cys Val Arg Arg Leu Val Leu Ala Thr Leu Ala Ala
1               5                   10                  15

Val Val Ala Leu Leu Cys Thr Ser Ser Ala Pro Val Ala Arg Ala
            20                  25                  30

Ala Val Lys Asp Asp Phe Thr Ala Ala Gln Arg Thr Asn Thr Leu Ala
        35                  40                  45

Val Leu Glu Ala Phe Gly Arg Ala Ile Pro Glu Leu Gly Lys Leu Trp
    50                  55                  60

Lys Gly Asp Asp Phe Cys Phe Trp Glu Ser Val Val Arg Cys Asp
65                  70                  75                  80

Arg Ser Val Leu Gly Lys Ser Val Arg Arg Ile Pro Ala Arg Cys
                85                  90                  95

Arg Arg Cys Leu Trp Thr Ser Thr Thr Arg Pro Ser Trp Ser Ser Thr
            100                 105                 110

Ser Thr Phe Pro Lys Trp Gly Trp Gly Trp Ala Glu Arg Cys Arg Thr
        115                 120                 125

Ala Gly Ala Gly Cys Arg Asp Trp Pro His Leu Arg Cys Arg Ala Ala
    130                 135                 140

Ala Trp Ala Val Arg Cys Pro Pro Arg Gly Ala Arg Trp Ser Leu Trp
145                 150                 155                 160

Cys Arg Cys Gly Leu Arg Val Val Lys Val Leu Pro Ala Ser Cys Arg
                165                 170                 175

Leu Ser Gly Ala Arg Trp Asn Arg Trp Glu Ile Ser Ile Cys Met Ala
            180                 185                 190

Arg Arg Phe Pro Ala Arg Cys Arg Leu Ser Gly Ala Arg Trp Asn Arg
        195                 200                 205
```

Trp Pro Phe Ser Ile Cys Arg Thr Leu Arg Leu Pro Ala Val Cys Arg
    210                 215                 220

Leu Ser Gly Ala Gln Trp Asn Pro Trp Pro Phe Ser Val Trp Met Ala
225                 230                 235                 240

Arg Arg Phe Pro Ala Arg Cys His Pro Ser Gly Ala Arg Trp His Arg
                245                 250                 255

Trp Ala Phe Ser Val Trp Arg Val Leu Ser Ser Pro Ala Arg Tyr Arg
                260                 265                 270

Pro Ser Gly Ser Gly Met Thr Ser Leu Val Thr Leu Phe Leu Gln Gly
            275                 280                 285

Thr Gln Val Ser Gly Thr Leu Pro Pro Gln Trp Arg Ser Met Leu Asn
290                 295                 300

Ala Glu Phe Leu Gln Leu Glu Asn Cys Asp Leu Ser Gly Cys Leu Pro
305                 310                 315                 320

Pro Glu Trp Ala Ala Met Pro Lys Leu Arg His Val Glu Leu Lys Gly
                325                 330                 335

Asn Gln Phe Ala Gly Cys Val Pro Asp Ser Trp Ala Gln Lys Ala Gly
                340                 345                 350

Leu Val Val Glu Ile Glu Asp Lys His Thr Gly Asn Ser Cys Ile Ala
            355                 360                 365

Gly Ala Asp Cys Ala Thr Thr Thr Thr Thr Thr Glu Pro Thr Ser
370                 375                 380

Thr Ala Ser Pro Thr Ala Thr Pro Thr Ser Ala Pro Glu Thr Glu Cys
385                 390                 395                 400

Glu Val Asp Gly Cys Glu Val Cys Asp Gly Asp Ser Ala Ala Arg Cys
                405                 410                 415

Ala Arg Cys Arg Glu Gly Tyr Phe Leu Thr Asp Glu Arg Thr Cys Leu
                420                 425                 430

Val Tyr Arg Asp Gly Gly Val Ala Val Ser Ile Gly Ala Ala Ala
            435                 440                 445

Ala Ala Val Val Cys Met Ala Val Leu Leu Ser Val Gly Leu Ala Ala
    450                 455                 460

<210> SEQ ID NO 13
<211> LENGTH: 2333
<212> TYPE: DNA
<213> ORGANISM: Artificial sequence
<220> FEATURE:
<223> OTHER INFORMATION: Leishmania amazonensis promastigotes surface
      antigens

<400> SEQUENCE: 13
gacccctgtt gcgaatggcg cagtgcgtgc gtcggctggt gctggcggcg cccctcgccg      60
ctgtggtggc gctgctgctg tgcacgagca gtgcaccggt ggcgcgtgct gcggggacga     120
gcgacttcac tgaggcgcag cagacgaaca cgctgacggt gctgcaggcg tttgcgcgtg     180
cgatccctgc gcttggggac acgtggacgg gcagcgactt ctgctcgtgg aagcacatca     240
tctgcgactc ccccggcgtc ggcgtgtgga tgggcgatgt ggattatacc ggcacgctgc     300
cggagatgcc tgcgagcgtc gactacaagg acgtcatgat cacggaactg aacttcagcg     360
caatgggcca ggggctgagc gggacgctgc ccccctcatg gagctcgctg acgtccttga     420
tatcactgtg catcgaaaag tctgagaagg tcaccggcac gctgcctgcc cagtggagct     480
cgatgacgtc gctggacaac cttaacctgc acgacacggc ggtctccggc acgctgcctg     540
cccagtggag ctcgatgaag cagctgaccg ttctggatct ggaggggcact aaggtgtccg     600

```
gcacgctgcc gtccgagtgg agtgggatgg cgaaggccga ggccgtgcag ctggagaact    660
gcggtctgtc cgggagtctg cccccctcgt ggtctgcgat gccgaagctg cgtatcgtct    720
cactgagcgg caaccacttc tgcgggtgcg tgcccgactc gtggagggag aaggaccgcc    780
tcgatgtgac catcgaggaa tggcacatgg gcgaggactg caagcttgct aacgcctgcc    840
gcccgactgc tgctccggga acgaccacga ctaacccgcc caccaccacc ggcaccccag    900
cagcctcctc tactccttct ccagggtcgg ggtgcgaggt ggatgggtgt gaggtgtgcg    960
agggggactc cgctgcgcgg tgcgccaggt gccgtgaggg ctactccctg acggacgaga   1020
agacgtgcct ggcgaaccac gatgcgcgcg tggcggcggc gtcgagcgga gcggtggctg   1080
ccgctgctgt gtgggcggct gtgctgttga gcgtggggct ggtggcgtga gggtgcggcg   1140 ggccctctt ctctgtggtg ccctggtgc ctgccctcgc cccggcacg cgtcgtcgc       1200 tgccctctct cacccccacc agccgacggg gagaccgaca gccacacgcg cacgcgcaca   1260
cgccgtcgtg catcgcgtgt gctttccgcc gttgtggcgc ctgcacggat gcacgggcat   1320
gcggaggcgt gcatgcgtgt gcgcgtgcca gctcttgtgt gtctctccgt gtggccagca   1380
gtcggcaccc cgccgatcg aatgtgcgcg cggcggcggt gtgtcgccctt ggacagcgga   1440 tgcgggcgcc cgcccctcgc cgtgtgccct gcggtctgct gtgctgccgc cgagcgacg   1500 tacggatgcg ctgtccggcc ctcttcgacg gggctcgctt gcggtgctgt gctctcgtgg   1560
tctgtgccgg tgctgccctg gcggggtgag agctggcggg ggcgtgggtg cgcgcgcggc   1620
agctctccgc tgcgttgagg gcggcctgcc cctgcgtccg cgcaccgtcg cgctctcctc   1680
gacgccactg cgcgcgcttg ttggcttgct ttgctctgtc gtgcgcactc tctcttattt   1740
tccgtttcat tcgcctgtat tctcttctcc caccgcactg cggcctcgtc accgcggccg   1800
tgcggtgcgc aggcgggtga tgtgccgttg tgcccccccct ttcatggcgc gctgggccga   1860
tcgccctctt gcctccctcc tccccctccc cctcccgccg gtcctgtcaa ttgtatatcc   1920 gtggaccta tcttcgtact gcctccgcgc ctcttccgta aagcttcgtt ggcgtgtgcc   1980
gccccccgga cgtcagcgcc gctgtgctcg catgctcacg gtgcgtcccc gtgcgtgggc   2040
gtgcacgtaa ggacatgtat atatgtatgt gtatgtatat gagtatgtat atatgtacgg   2100
ttatatatag gaatttgtgt atgttgaggt gtatgcatgt gcgtgcgtat attagtgtgt   2160
gcgagcacgc gtgttgcgcc acgctctgct gcccgcctcc gctgtgcgtg tcactcgctg   2220
tgggcgcggt ggcgggtggc gccgggtggt ggccgtgcgg cgggcggggg ctcctctgtg   2280
tttctctatt tctctgttcc ctgttgacct caaaaaaaaa aaaaaaaaaa aaa           2333
```

<210> SEQ ID NO 14
<211> LENGTH: 84
<212> TYPE: DNA
<213> ORGANISM: Artificial sequence
<220> FEATURE:
<223> OTHER INFORMATION: Nucleotidic

<400> SEQUENCE: 14

```
atggcctcga ggctcgtccg tgtgctggcc gccgccatgc tggttgcagc ggccgtgtcg     60
gtcgacgctg gcgcctctct agac                                           84
```

<210> SEQ ID NO 15
<211> LENGTH: 96
<212> TYPE: DNA
<213> ORGANISM: Artificial sequence
<220> FEATURE:
<223> OTHER INFORMATION: Nucleotidic

<400> SEQUENCE: 15

```
atggcgctgt gcgtgcgtcg gctggtgctg gcggcgaccc tcgccgctgt ggtggcgctg      60
ctgctgtgca cgagcagtgc gccggtggcg cgtgct                                96
```

<210> SEQ ID NO 16
<211> LENGTH: 96
<212> TYPE: DNA
<213> ORGANISM: Artificial sequence
<220> FEATURE:
<223> OTHER INFORMATION: Nucleotidic

<400> SEQUENCE: 16

```
atggcgcagt gcgtgcgtcg gctggtgctg gcggcgcccc tcgccgctgt ggtggcgctg      60
ctgctgtgca cgagcagtgc accggtggcg cgtgct                                96
```

<210> SEQ ID NO 17
<211> LENGTH: 1404
<212> TYPE: DNA
<213> ORGANISM: Artificial sequence
<220> FEATURE:
<223> OTHER INFORMATION: Nucleotidic

<400> SEQUENCE: 17

```
atggcgctgt gcgtgcgtcg gctggtgctg gcggcgaccc tcgccgctgt ggtggcgctg      60
ctgctgtgca cgagcagtgc gccggtggcg cgtgctgctg tgaaggatga cttcactgct     120
gcgcagcgga cgaacacgct ggcggtgctg gaggcgtttg gcgtgcgat ccctgagctt     180
gggaagctgt ggaagggcga cgacttctgc ttttgggagt cggtcgtgtg cgatgtgacc     240
gaagtgtact tgtgggaaat cggtgcgacg tataccggca cgctgccgga gatgcctgtg     300
gacgtcgact acacggccgt catggtcaag cacctcgact ttcccaaat ggggctgggg     360
ctgagcggaa cgctgccgga cagctggagc aggctgcagg gactgacctc acttacgttg     420
tcgggctgcg gcgtgagcgg tacgctgccc ccctcgtggc gctcgatgaa gtctttggtg     480
tcgttgtgga ttgagagttg tgaaagtgtt accggcaagc tgccgcctga gtggagctcg     540
atgaaatcgc tgagagatct ccatctgcat ggcgcgaagg tttccggcac gctgccgcct     600
gagtggagca cgatgaaatc gctgacccct tctcgatctgc aggacactca ggttaccggc     660
agtctgccgc ctgagtggag ctcaatgaaa tccatgacca ttctcagtct gaatggcgcg     720
aaggtttccg gcacgctgcc accccagtgg agctcgatga catcgctgag ccttctcagt     780
ctggagggta ctcagctctc cggcacgcta ccgccccagt ggagtgggat gacatcgctg     840
gtcacgcttt ttctgcaggg tactcaggtc tccggcactc tgccgccgca gtggagatcg     900
atgttgaatg ccgagttcct gcagctggag aactgcgacc tgtccggctg tttgccccc     960
gagtgggctg cgatgccgaa gctgcgtcat gtcgaactta agggcaacca gttcgccggg    1020
tgtgtgccgg actcgtgggc tcagaaggcc ggtctcgttg tggaaatcga ggataagcac    1080
acgggcaaca gctgcattgc tggtgcggac tgcgcaacga cgaccacgac caccactgaa    1140
cccacgtcca ctgcgagccc aacagccacg cctacctctg cccccgagac ggagtgcgag    1200
gtggatgggt gtgaggtgtg cgatgggac tccgcggcga ggtgcgccag gtgccgtgag    1260
ggctacttcc tgacggacga gaggacgtgc ctggtgtacc gcgatggcgg cgttgtggcc    1320
gtgtcgatcg agcggctgc tgccgctgtt gtgtgcatgg ctgtgctgct gagcgtgggg    1380
ctggcggcgt gaggatgccg ctgc                                           1404
```

```
<210> SEQ ID NO 18
<211> LENGTH: 462
<212> TYPE: PRT
<213> ORGANISM: Artificial sequence
<220> FEATURE:
<223> OTHER INFORMATION: Protein

<400> SEQUENCE: 18

Met Ala Leu Cys Val Arg Arg Leu Val Leu Ala Ala Thr Leu Ala Ala
1               5                   10                  15

Val Val Ala Leu Leu Cys Thr Ser Ser Ala Pro Val Ala Arg Ala
            20                  25                  30

Ala Val Lys Asp Asp Phe Thr Ala Ala Gln Arg Thr Asn Thr Leu Ala
        35                  40                  45

Val Leu Glu Ala Phe Gly Arg Ala Ile Pro Glu Leu Gly Lys Leu Trp
    50                  55                  60

Lys Gly Asp Asp Phe Cys Phe Trp Glu Ser Val Val Cys Asp Val Thr
65                  70                  75                  80

Glu Val Tyr Leu Trp Glu Ile Gly Ala Thr Tyr Gly Thr Leu Pro
                85                  90                  95

Glu Met Pro Val Asp Val Asp Tyr Thr Ala Val Met Val Lys His Leu
            100                 105                 110

Asp Phe Ser Gln Met Gly Leu Gly Leu Ser Gly Thr Leu Pro Asp Ser
        115                 120                 125

Trp Ser Arg Leu Gln Gly Leu Thr Ser Leu Thr Leu Ser Gly Cys Gly
    130                 135                 140

Val Ser Gly Thr Leu Pro Pro Ser Trp Arg Ser Met Lys Ser Leu Val
145                 150                 155                 160

Ser Leu Trp Ile Glu Ser Cys Glu Ser Val Thr Gly Lys Leu Pro Pro
                165                 170                 175

Glu Trp Ser Ser Met Lys Ser Leu Arg Asp Leu His Leu His Gly Ala
            180                 185                 190

Lys Val Ser Gly Thr Leu Pro Pro Glu Trp Ser Thr Met Lys Ser Leu
        195                 200                 205

Thr Leu Leu Asp Leu Gln Asp Thr Gln Val Thr Gly Ser Leu Pro Pro
    210                 215                 220

Glu Trp Ser Ser Met Lys Ser Met Thr Ile Leu Ser Leu Asn Gly Ala
225                 230                 235                 240

Lys Val Ser Gly Thr Leu Pro Pro Gln Trp Ser Ser Met Thr Ser Leu
                245                 250                 255

Ser Leu Leu Ser Leu Glu Gly Thr Gln Leu Ser Gly Thr Leu Pro Pro
            260                 265                 270

Gln Trp Ser Gly Met Thr Ser Leu Val Thr Leu Phe Leu Gln Gly Thr
        275                 280                 285

Gln Val Ser Gly Thr Leu Pro Pro Gln Trp Arg Ser Met Leu Asn Ala
    290                 295                 300

Glu Phe Leu Gln Leu Glu Asn Cys Asp Leu Ser Gly Cys Leu Pro Pro
305                 310                 315                 320

Glu Trp Ala Ala Met Pro Lys Leu Arg His Val Glu Leu Lys Gly Asn
                325                 330                 335

Gln Phe Ala Gly Cys Val Pro Asp Ser Trp Ala Gln Lys Ala Gly Leu
            340                 345                 350

Val Val Glu Ile Glu Asp Lys His Thr Gly Asn Ser Cys Ile Ala Gly
        355                 360                 365
```

Ala Asp Cys Ala Thr Thr Thr Thr Thr Thr Glu Pro Thr Ser Thr
370                 375                 380

Ala Ser Pro Thr Ala Thr Pro Ser Ala Pro Glu Thr Glu Cys Glu Val
385                 390                 395                 400

Asp Gly Cys Glu Val Cys Asp Gly Asp Ser Ala Ala Arg Cys Ala Arg
                405                 410                 415

Cys Arg Glu Gly Tyr Phe Leu Thr Asp Glu Arg Thr Cys Leu Val Tyr
                420                 425                 430

Arg Asp Gly Gly Val Val Ala Val Ser Ile Gly Ala Ala Ala Ala
                435                 440                 445

Val Val Cys Met Ala Val Leu Leu Ser Val Gly Leu Ala Ala
450                 455                 460

<210> SEQ ID NO 19
<211> LENGTH: 1338
<212> TYPE: DNA
<213> ORGANISM: Artificial sequence
<220> FEATURE:
<223> OTHER INFORMATION: Nucleotidic

<400> SEQUENCE: 19
ggatccatgc atcaccatca ccatcacgcg ctgtgcgtgc gtcggctggt gctggcggcg      60
accctcgccg ctgtggtggc gctgctgctg tgcacgagca gtgcgccggt ggcgcgtgct     120
gctgtgaagg atgacttcac tgctgcgcag cggacgaaca cgctggcggt gctggaggcg     180
tttgggcgtg cgatccctga gcttgggaag ctgtggaagg cgacgacttc tgctttttgg     240
gagtcggtcg tgtgcgatgt gaccgaagtg tacttgtggg aaatcggtgc gacgtatacc     300
ggcacgctgc cggagatgcc tgtggacgtc gactacacgg ccgtcatggt caagcacctc     360
gacttttccc aaatggggct ggggctgagc ggaacgctgc cggacagctg gagcaggctg     420
cagggactga cctcacttac gttgtcgggc tgcggcgtga gcggtacgct gccccccctcg    480 tggcgctcga tgaagtctttt ggtgtcgttg tggattgaga gttgtgaaag tgttaccggc    540
aagctgccgc ctgagtggag ctcgatgaaa tcgctgagag atctccatct gcatggcgcg     600
aaggtttccg gcacgctgcc gcctgagtgg agcacgatga aatcgctgac ccttctcgat     660
ctgcaggaca ctcaggttac cggcagtctg ccgcctgagt ggagctcaat gaaatccatg     720
accattctca gtctgaatgg cgcgaaggtt tccggcacgc tgccacccca gtggagctcg     780
atgacatcgc tgagccttct cagtctggag ggtactcagc tctccggcac gctaccgccc     840
cagtggagtg ggatgacatc gctggtcacg ctttttctgc agggtactca ggtctccggc     900
actctgccgc cgcagtggag atcgatgttg aatgccgagt cctgcagct ggagaactgc      960 gacctgtccg ctgtttgcc cccgagtgg gctgcgatgc cgaagctgcg tcatgtcgaa      1020
cttaagggca accagttcgc cgggtgtgtg ccggactcgt gggctcagaa ggccggtctc     1080
gttgtggaaa tcgaggataa gcacacgggc aacagctgca ttgctggtgc ggactgcgca     1140
acgacgacca cgaccaccac tgaacccacg tccactgcga gcccaacagc cacgcctacc     1200 tctgccccg agacggagtg cgaggtggat gggtgtgagg tgtgcgatgg ggactccgcg      1260
gcgaggtgcg ccaggtgccg tgagggctac ttcctgacgg acgagaggac gtgcctggtg     1320
taccgcgatt gagagctc                                                  1338

<210> SEQ ID NO 20
<211> LENGTH: 2063
<212> TYPE: DNA
<213> ORGANISM: Artificial sequence
<220> FEATURE:
<223> OTHER INFORMATION: Nucleotidic

<400> SEQUENCE: 20

```
aattcgagct cggtacccat cgtacccta ctccaaaaat gtcaaagata cagtctcaga        60
agaccaaagg gctattgaga cttttcaaca aagggtaatt tcgggaaacc tcctcggatt      120
ccattgccca gctatctgtc acttcatcga aaggacagta gaaaggaag gtggctccta      180
caaatgccat cattgcgata aaggaaaggc tatcattcaa gatgcctctg ccgacagtgg      240
tcccaaagat ggacccccac ccacgaggag catcgtggaa aagaagacg ttccaaccac       300
gtcttcaaag caagtggatt gatgtgacat ctccactgac gtaagggatg acgcacaatc      360
ccactatcct tcgcaagacc cttcctctat ataaggaagt tcatttcatt tggagaggac      420
agcccaagct tggatccatg catcaccatc accatcacgc gctgtgcgtg cgtcggctgg      480
tgctggcggc gaccctcgcc gctgtggtgg cgctgctgct gtgcacgagc agtgcgccgg      540
tggcgcgtgc tgctgtgaag gatgacttca ctgctgcgca gcggacgaac acgctggcgg      600
tgctggaggc gtttgggcgt gcgatccctg agcttgggaa gctgtggaag ggcgacgact      660
tctgcttttg ggagtcggtc gtgtgcgatg tgaccgaagt gtacttgtgg gaaatcggtg      720
cgacgtatac cggcacgctg ccggagatgc ctgtggacgt cgactacacg gccgtcatgg      780
tcaagcacct cgactttcc caatgggggc tggggctgag cggaacgctg ccggacagct       840
ggagcaggct gcagggactg acctcactta cgttgtcggg ctgcgcgtg agcggtacgc       900
tgcccccctc gtggcgctcg atgaagtctt tggtgtcgtt gtggattgag agttgtgaaa      960
gtgttaccgg caagctgccg cctgagtgga gctcgatgaa atcgctgaga gatctccatc     1020
tgcatggcgc gaaggtttcc ggcacgctgc cgcctgagtg gagcacgatg aaatcgctga     1080
cccttctcga tctgcaggac actcaggtta ccggcagtct gccgcctgag tggagctcaa     1140
tgaaatccat gaccattctc agtctgaatg gcgcgaaggt ttccggcacg ctgccacccc     1200
agtggagctc gatgacatcg ctgagccttc tcagtctgga gggtactcag ctctccggca     1260
cgctaccgcc ccagtggagt gggatgacat cgctggtcac gctttttctg cagggtactc     1320
aggtctccgg cactctgccg ccgcagtgga gatcgatgtt gaatgccgag ttcctgcagc     1380
tggagaactg cgacctgtcc ggctgtttgc cccccgagtg ggctgcgatg ccgaagctgc     1440
gtcatgtcga acttaagggc aaccagttcg ccgggtgtgt gccggactcg tgggctcaga     1500
aggccggtct cgttgtggaa atcgaggata agcacacggg caacagctgc attgctggtg     1560
cggactgcgc aacgacgacc acgaccacca ctgaacccac gtccactgcg agcccaacag     1620
ccacgcctac ctctgccccc gagacggagt gcgaggtgga tgggtgtgag gtgtgcgatg     1680
gggactccgc ggcgaggtgc gccaggtgcc gtgagggcta cttcctgacg gacgagagga     1740
cgtgcctggt gtaccgcgat tgagagctcg aattcggtac gctgaaatca ccagtctctc     1800
tctacaaatc tatctctctc tattttctcc ataaataatg tgtgagtagt ttcccgataa     1860
gggaaattag ggttcttata gggtttcgct catgtgtaag catataagaa acccttagta     1920
tgtatttgta tttgtaaaat acttctatca ataaaatttc taattcctaa aaccaaaatc     1980
cagtactaaa atccagatcg atggggatcc tctagagtcg acctgcaggc atgcaagctt     2040
ggcactggcc gtcgttttac aac                                              2063
```

MEANS FOR THE TRANSIENT PRODUCTION IN PLANTS OF RECOMBINANT PROTEINS THAT CAN BE USED IN PARTICULAR IN PROPHYLAXIS AND IN THERAPEUTICS

CROSS-REFERENCE TO RELATED APPLICATIONS

This application is a national stage application under 35 U.S.C. §371 of PCT/IB2011/052288, filed May 26, 2011, which claims benefit of French application 1002204, filed May 26, 2010.

SEQUENCE LISTING

A Sequence Listing associated with this application is filed in electronic format via EFS-Web and hereby is incorporated by reference into the specification. The name of the text file containing the Sequence Listing is REPLACEMENT_SEQUENCE_LISTING_21029-00413_ST25.txt. The size of the text file is 48 kb, and the text file was created on Nov. 19, 2012.

The invention relates to means for the transient production in plants of recombinant proteins of interest and to applications of the recombinant proteins obtained, in particular in the field of human and animal health.

Within the description and the claims, the term "recombinant proteins of interest" is understood to refer to biologically active proteins, in particular for preventive or curative use, that are obtained by genetic recombination techniques.

The classic systems for producing recombinant proteins of biological interest include bacteria, yeasts and mammalian or insect cells. Yields of 1 to 3 g/l are obtained for example from mammalian cell suspensions.

The yields are generally lower in plants, specifically in the order of 100 to 200 mg/l, but the production costs appear to be markedly lower.

The large-scale production of recombinant proteins requires a number of constraints to be taken into account, among them the post-transcriptional regulation mechanism, commonly referred to by the abbreviation PTGS, which stands for post-transcriptional gene silencing.

This mechanism, which generally comes into play in a viral infection, limits the expression of recombinant proteins, specifically by degrading the mRNAs that code for these proteins.

The co-expression of silencing suppressor proteins at the same time as the protein to be produced has been proposed as a way of addressing this problem.

The work of the inventors has focused more specifically, within this context, on obtaining means of achieving a high level of expression of an antigen protein of *Leishmania* promastigotes or amastigotes.

Surprisingly, the research that was undertaken showed that the use of a mixture of silencing suppressors greatly increased the expression of the antigen protein. Advantageously, such effects are likewise obtained in general terms with other proteins of interest.

The object of the invention is therefore to provide a composition for the transfection of an agrobacterium for the purpose of inoculation in a plant in order to co-express a protein of interest with a mixture of silencing suppressors.

The object of the invention is more specifically to provide means for the co-expression of an antigen protein of *Leishmania* promastigotes or amastigotes.

It also seeks to provide a method of production, in a transient system, of an antigen protein of *Leishmania* promastigotes or amastigotes in a plant, which is suitable for use on an industrial scale, more specifically of a promastigote surface antigen (PSA) or a PSA derivative.

The invention thus firstly provides a composition for the inoculation in a plant of agrobacteria transfected by expression vectors, in order to produce in said plant a protein of interest or a derivative of said protein, by deletion or by mutation, characterised in that it comprises
    agrobacteria transfected by at least one expression vector, comprising a nucleotide sequence insert that codes for said protein or a derivative of said protein, and
    agrobacteria transfected by a plurality of expression vectors, each comprising at least one nucleotide sequence insert that codes for proteins having a silencing suppressor effect.

Surprisingly, the mixture of silencing suppressors leads to a synergistic silencing effect, allowing high yields of proteins or protein derivatives to be obtained.

In accordance with this first aspect, the invention more specifically provides a composition for the inoculation in a plant of agrobacteria transfected by expression vectors, in order to produce in said plant a PSA or a PSA derivative, by deletion or by mutation, characterised in that it comprises
    a) agrobacteria transfected by at least one expression vector, comprising a nucleotide sequence insert that codes for said PSA or a PSA derivative, and
    b) agrobacteria transfected by a plurality of expression vectors, each comprising at least one nucleotide sequence insert that codes for proteins having a silencing suppressor effect.

The nucleotide sequence inserted in vector a) advantageously corresponds to one of the sequences SEQ ID NO: 1-5 and 11, described in particular in the application WO 2005/051989 submitted by IRD.

These sequences are capable of coding for PSAs of, respectively, sequences SEQ ID NO: 6-10 and 12.

More particularly, the nucleotide sequence inserted in vector a) corresponds to that of the IJ11 gene of *L. infantum* of sequence SEQ ID NO: 11, which codes for the LiPSA 50s protein of sequence SEQ ID NO: 12, or of the cDNA clone A3B of *L. amazonensis* of sequence SEQ ID NO: 13.

In other nucleotide sequences one or more codons has been deleted or mutated in the above sequences. The proteins encoded by such sequences correspond to PSA derivatives which can likewise be produced in a plant, in accordance with the invention.

According to an advantageous embodiment, which stimulates production of PSA or the PSA derivative, the vector in a) comprises upstream of the nucleotide sequence and downstream of the promoter a nucleotide sequence that codes for a *Leishmania* secretion/excretion signal peptide (SP).

Examples are the sequences SEQ ID NO: 14-16, which code respectively for the signal peptide of the PSA of *L. mexicana, L. infantum* (encoded by the IJ11 gene) or *L. amazonensis* (encoded by the cDNA clone A3B):
The sequences SEQ ID NO: 14-16 are as follows:

SEQ ID NO: 14:
ATGGCCTCGAGGCTCGTCCGTGTGCTGGCCGCCGCCATGCTGGTTGCA
GCGGCCGTGTCGGTCGACGCTGGCGCCTCTAGAC

SEQ ID NO: 15:
ATGGCGCTGTGCGTGCGTCGGCTGGTGCTGGCGGCGACCCTCGCCGCT
GTGGTGGCGCTGCTGCTGTGCACGAGCAGTGCGCCGGTGGCGCGTGCT

-continued

SEQ ID NO: 16:
ATGGCGCAGTGCGTGCGTCGGCTGGTGCTGGCGGCGCCCCTCGCCGCT
GTGGTGGCGCTGCTGCTGTGCACGAGCAGTGCACCGGTGGCGCGTGCT

The sequences inserted in the expression vectors in b) advantageously correspond to sequences that code for proteins expressed by viruses responsible for plant diseases, such as sobemoviruses, poleroviruses or nepoviruses, or for mutants of said proteins. Proteins having a strong silencing suppressor effect correspond to those expressed by RYMV (rice yellow mottle virus), IYMV (Imperata yellow mottle virus), BWYV (beet western yellows virus) or TRSV (tomato ringspot virus).

Alternatively it can be a mutant of sequences that code for these proteins, in which a wild-type codon has been modified.

Preferred nucleotide sequences correspond to those that code for an RYMV or IYMV P1 suppressor protein, which is also responsible for cell-to-cell movement in the plant, or a mutant of such a protein.

Thus the RYMV ORF1 codes for a silencing suppressor protein having a molecular weight of 18-19 kDa (Voinnet et al, 1999; Siré et al, 2008). The P1 protein expressed according to the invention preferably corresponds to that of an isolate from Tanzania designated by P1-Tz3, such as described in Siré et al, 2008 cited above.

Preferred nucleic acid sequences that have been modified by mutation include wild-type sequences in which the GCC codon in position 58 has been replaced by the ACC codon, and/or the AAG codon in position 160 has been replaced by the GGG codon and the CAG codon in position 196 by the GAC codon.

The corresponding mutant nucleic acids are referred to in the description and the claims as P1-A20T, P1-K54G, P1-Q66R, P1-Q110D.

These nucleotide sequences are capable of coding for proteins including wild-type sequences in which Ala in position 20 has been replaced by Thr, Lys in position 54 by Gly, Gln in position 66 by Arg and Gln in position 110 by Asp.

The above nucleic acids can include several mutations. For example, a nucleic acid of this preferred type includes the first three mutations above and thus corresponds to P1 A20T-K54G-Q66.

A preferred nucleic acid sequence of IYMV codes for a P1 protein having a molecular weight of 24.1 kDa (Sérémé et al. 2008).

Other nucleotide sequences code for suppressor proteins acting at different levels of the silencing pathway, such as the BWYV PO protein and the TRSV P19 protein.

The invention secondly provides a method of producing a protein of interest or a derivative of a protein of interest in a plant, characterised by the co-expression, in the plant, of the protein of interest or the derivative of said protein and a mixture of proteins having a silencing suppressor effect, by expression vectors such as defined above.

In particular the invention provides a method of producing PSA or a PSA derivative in a plant, characterised by the co-expression, in the plant, of the PSA or PSA derivative and a mixture of proteins having a silencing suppressor effect, by the expression vectors defined in a) and b) above.

More particularly, said method comprises
transfection of agrobacteria by the inoculation composition with said expression vectors,
agroinfiltration of the host plant by the mixture of agrobacteria obtained in the preceding step, and
extraction of the biologically active protein.

The agroinfiltration step is advantageously performed using a ratio of the agrobacteria strains expressing PSA to the mixture of strains expressing suppressors of in particular 45:55 to 55:45 and more specifically 50:50.

According to another advantageous embodiment, the strains expressing the suppressors correspond more specifically to a mixture of strains transfected by nucleotide sequences that code for RYMV P1-TZ3 or IYMV P1, or mutants of P1-TZ3 such as P1-Q66R or P1-A20T or P1-Q66R, and strains transfected by nucleotide sequences that code for BWYV P0 or TRSV P19.

The strains transfected by nucleotide sequences that code for mutants of proteins having a suppressor effect include one or more mutants of the same protein or a protein having multiple mutations.

For example, a preferred combination, for the transient expression in *N. benthamiana*, includes P0 of BWYMV+ P1x+P19, where x corresponds to a mutant of P1 and is an integer from 1 to 3.

In the above combination the strains are advantageously each present in the ratio 1:3.

The extraction step comprises grinding the leaves of the plant several days after transfection, more particularly 6 days after transfection, using an extraction buffer and a centrifuging step, followed by recovery of the protein extract, which is then subjected to one or more purification steps.

According to one embodiment, the PSA is purified in a nickel column. As histidine residues have a very strong affinity for nickel, a tail of multiple His residues, for example 10, is added at the N terminus of the PSA.

In a preferred embodiment of the invention, the agrobacterium is *Agrobacterium tumefaciens*.

The host plant is advantageously tobacco, in particular *N. benthamiana*.

The above embodiments can be used to produce the protein of interest with a His sequence for purification and at an expression level in the order of 100 mg/kg of fresh leaves.

In particular, we assess the benefit of obtaining in this way a PSA or a PSA derivative, in significant quantities, for use in prophylaxis and in human or animal medicine.

In general terms the invention provides the means of developing new strategies for combatting infection processes.

Further characteristics and advantages of the invention are provided in the following examples, which make reference to FIGS. 1 to 9 as follows:

FIG. 1: Structure of the pCambia5300 plasmid used for the transformations according to the invention of *Agrobacterium tumefaciens*

Figure 2:
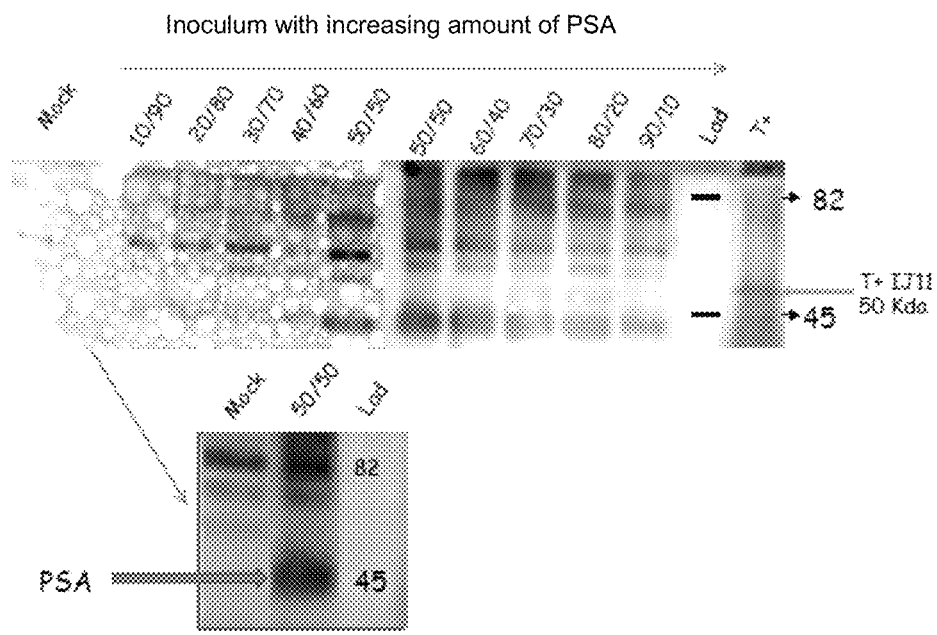

FIG. 2: Western blot showing the effects on PSA production of increasing the percentage of PSA strains relative to the percentage of suppressor strains FIG. 3: Western blot showing the results of PSA production using one or more suppressors FIG. 4: Effect of suppressor mutants FIG. 5: Estimate of the PSA yield FIG. 6: Effect of a mixture of various P1 on PSA expression FIG. 7: Effect of IYMV P1 in a mixture of suppressors FIG. 8: Results of PSA production FIG. 9: Construction of pCambia 1300 modified with the K7 insert cloned with BamH1 and SacI; the gene that codes for PSA IJ11 (IJ11 insert) is shown with the secretion-excretion sequence (sp+) and without the hydrophobe sequence (h−) located at the C terminus cloned with Bamh1 and Sac1 in pCambia 1300. Underlined sequences: A4; italic sequence before insert: 35S promoter, sequence after insert: nos terminator.

MATERIALS AND METHODS

I. Material

Plant Material

The tobacco that was used is the *Nicotiana benthamiana* RDR6 cultivar (Sainsbury Laboratory): it is a transgenic plant mutated in the silencing amplification pathway.

The tobacco is stored in bioclimatic chambers in a controlled atmosphere (22° C., 10 hours in the dark, 70% relative humidity).

The seedlings are pricked out two weeks after being sown, then agroinfiltrated after two weeks.

50 plants are used for each experiment.

Plasmid pCAMBIA 5300 is used to insert the genes that code for the proteins of interest. Its structure is shown in FIG. 1.

Transformation Vector:

*Agrobacterium tumefaciens* (strain GV3101)

Gene Coding for PSA:

*Leishmania* IJ11 gene coding for a protein excreted/secreted by *L. infantum,* 8M 56 kDA.

II. Production a—Plasmid Constructions

The gene that codes for the protein of interest is inserted between the P35S promoter and the T35S terminator of pCambia 5300.

b—Transformation of *Agrobacterium tumefaciens* by Means of These Constructions

The integration of plasmid DNA into *Agrobacterium tumefaciens* is carried out by electroporation (Biorad Gene Pulser system). An electric current is applied, which disrupts the bacterial wall, allowing DNA to penetrate.

The transformation product is spread over a selective medium (LB with the addition of 50 μg/ml rifampicin and 50 μg/ml kanamycin) and the cultures are incubated for 2 to 3 days at 28° C.

The positive colonies are cultured in a liquid medium and aliquots are taken in the presence of glycerol before being stored at −80° C.

c—Preparation of Agrobacterium Suspensions

The agrobacteria are cultured at 28° C. in a nutrient medium, LB with added rifampicin and kanamycin, for approximately 14 h to activate growth of the bacterial population. This preculture is then used to inoculate a larger volume of medium.

A volume of 50 ml per 3 plants is used for the agroinfiltration of 3 whole leaves.

At DO600=0.5 the physiological state of the bacteria appears optimal for agroinfiltration and the cultures are stopped.

After centrifuging (5 min at 4000 g), the bacteria are resuspended in the same volume of $MgCl_2$ 10 mM with addition of 200 μM acetosyringone. This mixture is used for transformation of the tobacco plants.

d—Preparation of Inocula:

The suspensions of *Agrobacterium tumefaciens* transformed by the plasmid constructions are mixed together.

Two types of mixture:

The mixtures obtained are designated below by reference to the protein types that are encoded by the strains of *Agrobacterium tumefaciens:*

PSA strain/mixture of suppressor strains

Mock: empty A4K7/mixture of suppressor strains

The mixture is allowed to rest for approximately 14 h at ambient temperature.

e—Agroinfiltration of Agrobacterium in *N. benthamiana* RDR6 Plants

Agrofiltrations are prepared using a syringe containing the inoculum.

The injection is performed on the abaxial surface of the leaf where the tissue is more capable of absorbing liquid. The plants are then returned to the bioclimatic chambers. The transformed leaves are harvested 6 days after agroinfiltration.

III. Extraction and Protein Assay by Spectrophotometry

The following extraction buffer is prepared:

Tris 20 mM

NaCl 300 Mm

Glucose 25 Mm

Triton™ non-ionic surfactant 1%

Glycerol 5%

DTT 5 mM

Antiprotease (EDTA-free)

Samples obtained from the transformed plants are frozen in liquid nitrogen and then ground. Nine leaves are ground for each treatment. The extraction buffer is added to the powder obtained by grinding.

The mixture is incubated for half an hour in ice, vortexing it from time to time. The tubes are centrifuged for 20 min, at 10,000 g and 4° C. The supernatant containing the proteins is recovered and each sample is assayed by the Bradford method, which involves mixing Coomassie Blue with the protein extract and measuring the absorption of the mixture at a wavelength of 595 nm.

IV. Immunodetection of PSA by Western Blot

1 Preparation of 12% Acrylamide Gels (19:1)

| | For 1 × 1.5 mm gel | |
|---|---|---|
| | Electrophoresis buffer, 12% | Concentrated gel, 5% |
| Acrylamide bis-acrylamide 40% | 3 ml | 500 μl |
| Tris HCl 1.5M, pH 8.8 | 2.6 ml | 500 μl |
| SDS 20% | 50 μl | 20 μl |
| Ammonium persulfate 10% | 100 μl | 40 μl |
| Temed ($N,N,N^1N^1$-tetramethylenediamine) | 10 μl | 4 μl |
| $H_2O$ | 4.4 ml | 3 ml |

Migration in an SDS-PAGE Gel

The samples are placed in a 12% acrylamide gel (19:1) using a glycerol+bromophenol blue+SDS buffer. The same amount of protein is placed in each well. Migration takes place in a TG-SDS 1X buffer.

The proteins are transferred to a PVDF membrane placed on the gel and an electric current crossing the gel in the direction of the membrane is applied. This step takes place in a transfer buffer (tris base 4.84 g; glycine 22.52 g; methanol 100 ml, $H_2O$ up to 2 1). The proteins, which were negatively charged by the SDS and previously separated by molecular weight, are entrained by the current and deposited on the membrane, which is detected by a polyclonal anti-PSA antibody.

The membrane is saturated with 5% skimmed milk (Biorad) in TBS 1X (tris base (20 mM): 2.423 g, NaCl (75 mM): 4.39 g, $H_2O$: to 1 1) for one hour at ambient temperature.

10 ml of this blocking solution are recovered, then the primary anti-PSA antibody (1/2000) is added. The membrane is left in this solution containing the antibody for approximately 14 h at 4° C., while stirring slowly.

The membrane is then recovered and washed as follows: 6 rinses of 2 min each with TBS-TWEEN® polysorbate (TBS-T=TBS 1X+500 μl TWEEN® 20polysorbate).

A secondary anti-rabbit antibody (1/10000) is added to a new blocking solution (1 μl in 10 ml) and the solution obtained is left for 1 hour at ambient temperature while stirring.

The membrane is then washed as follows: 4×2 min with TBS-T then 2×2 min with TBS 1X.

For the detection phase an ECL+(Enhanced Chemiluminescence) solution (Amersham), placed on the membrane, induces the enzymatic generation of an acridinium ester. The membrane is left for 5 min at ambient temperature. The result is obtained by scanning the membrane (Typhoon, Amersham) with the following parameters: scan at 100 μ, PMT=600, filter=520 BP 40. Emission wavelength=45 nm.

V. Construction for Purification of the Protein Produced

The pCambia 1300 vector modified with a K7 insert is used as the base vector. The insert of PSA (Ij11)sp+h-tagged at N terminus, with 6 histidines of 1326 pb or 442 aa (48.6 kDa protein), is cloned in A4K7 (pCambia 1300 modified with K7 insert) cloned with BamHI and SacI (FIG. 9 with diagram of insert), where italics=PSA IJ11 insert, normal font=pCambia vector, bold=Histag (according to ATG) and underlined: start=35S sequence and end: nos terminator).

SEQ ID NO: 19 corresponds to the insert sequence and SEQ ID NO: 20 to pCambia 1300 modified with the K7 insert, cloned with BamH1 and SacI.

RESULTS

Experiment 1

Study of Different Ratios of PSA Strains to Suspensor Strains

The conditions used are as follows:

3 plants per treatment, an inoculation of 3 leaves per plant and sampling on D+6, 20 μg of total extract are placed in each well.

An agrobacterium with an empty A4 vector (Mock)+mixture of suppressor strains is used as a control.
The mixture of suppressors is as follows: (⅓ P1+⅓ P0+⅓ P19)
D=days after agroinfiltration
PSA: sp+h-construction in GV3101
Conditions: non-denaturing for samples (no heating, no DTT)

Antibody: anti-ESP Ldi IJ11 sense 1/2000 (ESP =excreted/secreted protein)

PSA positive control: IJ11, *Leishmania* supernatant
Inocula with increasing amounts of PSA strain were used.

The results obtained by Western blot are shown in FIG. 2. The bands observed in the Mock (negative control in the experiment) are said to be aspecific and represent background noise.

The bands that appear only in the treatments and not in the Mock are assumed to correspond to the PSA. The intensity of the PSA bands is found to be the greatest in the 50/50 treatment. Under the experimental conditions this combination thus leads to the highest accumulation of PSA in the tobacco tissue.

Experiment 2

Figure 3:
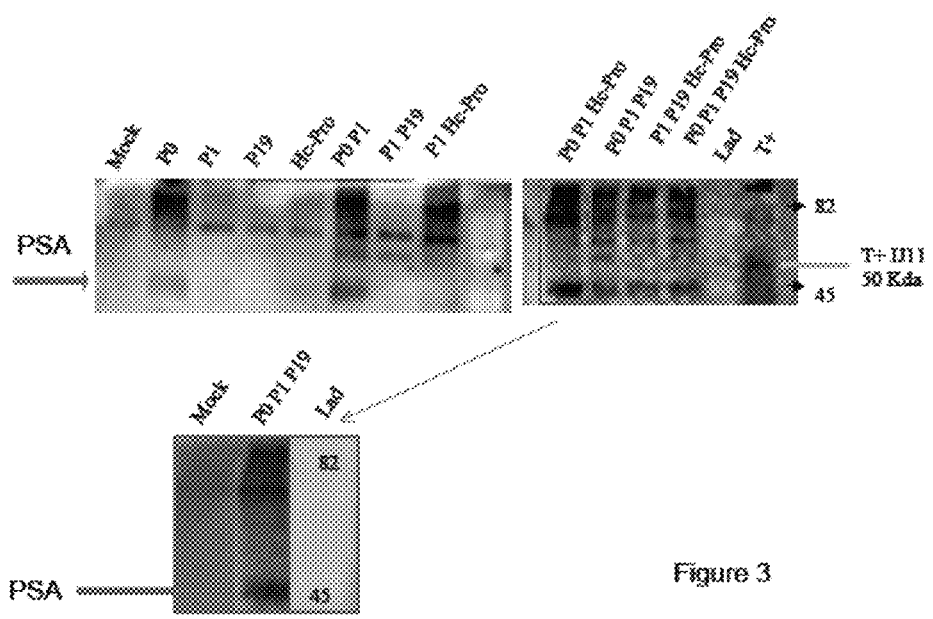

Study of the Effects on PSA Production of Suppressors used Alone or in Combination The results set out below are obtained under the following conditions:

Use of 3 plants per treatment, sampling on D+6, inoculation of 3 leaves per plant The inoculum used consists of 50% suppressors and 50% PSA Suppressors: P0, P1, P19, HcPro 30 μg of total extract are placed in each well Mock: agrobacterium with empty A4 vector D=days after agroinfiltration Conditions: non-denaturing for samples (no heating, no DTT)

Antibody: anti-ESP Ldi IJ11 sense 1/2000
PSA positive control: IJ11, *Leishmania* supernatant
Lad=ladder
The results obtained are shown in FIG. 3.

The transient expression of the gene that codes for the protein of interest varies according to the silencing suppressor, which results in different modes of action on the PTGS pathway.

On its own, P0 results in a fairly strong PSA expression, while P1 and P19 on their own appear to induce a very weak signal. By contrast, when a mixture of the 3 suppressors is used, a very strong band is observed, corresponding to a significant accumulation of PSA.

The mixture of suppressors P0, P1 and P19 thus appears to be particularly effective in *N. benthamiana*. This result shows a synergistic effect of suppressor proteins, corresponding to different key stages of PTGS.

Experiment 3

Study of the Effect of P1 Mutants in the Mixture of Suppressors on PSA Production The results below relate to experiments performed with the inoculum consisting of 50% suppressors and 50% PSA, using 3 mutants of P1-Tz3, namely P1-A20T, P1-K54G, P1-Q66R.

Figure 4:
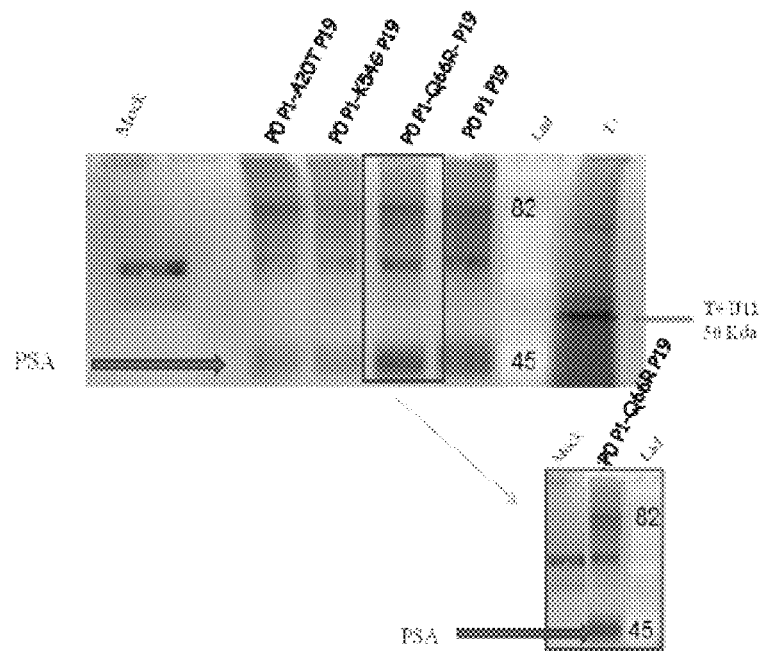
Figure 5:
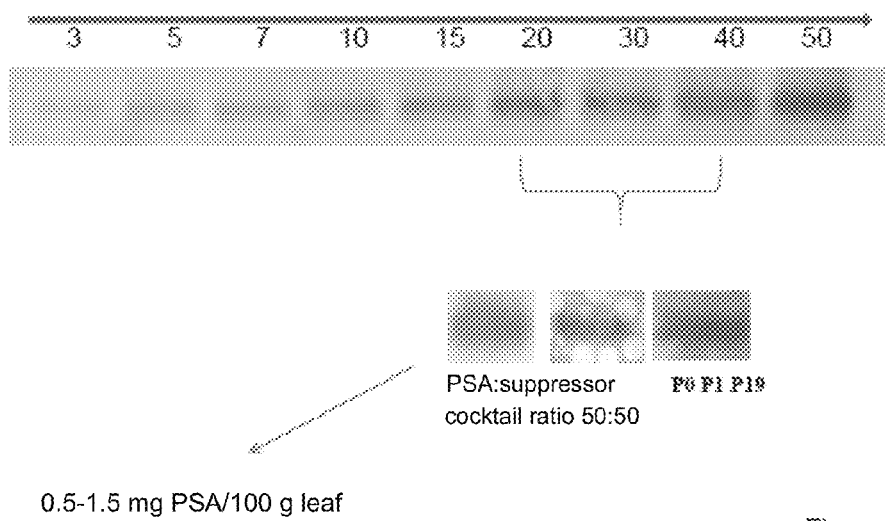

The conditions used correspond to those of experiments 1 and 2 and the symbols used in FIG. 4 have the same meanings.

The mixture of suppressors corresponds to ⅓ P0+⅓ P1x+⅓ P19, with different isolates or mutants of suppressor P1 being used (x). The mixture comprising P0 P1 P19 serves as a control and the P1 mixture is replaced in each inoculum by one of the mutants.

After Western blot detection, the mixture containing the mutant P1-Q66R is found to give a markedly more pronounced signal than that obtained with P1-A20T and P1-K54G.

In tobacco the combination P0, P 1-Q66R, P19 thus appears to be particularly effective in the transient expression of PSA.

Experiment 4

Estimate of the PSA Yield

The conditions used in this experiment are as follows:

3 plants per treatment, inoculation of 3 leaves per plant, sampling on D+6, antibody: anti-ESP Ldi IJ11 sense 1/2000

30 μg of total extract in each well inocula consist of: 50% PSA/50% mixture of suppressors mixture of suppressors: ⅓ P0+⅓ P1+⅓ P19

D=days after agroinfiltration

Conditions: non-denaturing for samples (no heating, no DTT)

Antibody: anti-ESP Ldi IJ11 sense 1/2000

Lad=ladder

The results are shown in FIG. 5.

The yield of PSA from 100 g of leaves is estimated at: 0.70 mg<PSA<1.40 mg.

Experiment 5

Mixture with Different P1, Sampling on D+6

The conditions used are those defined in Experiment 4 (T+=25 µl of *Leishmania* supernatant).

Figure 6:
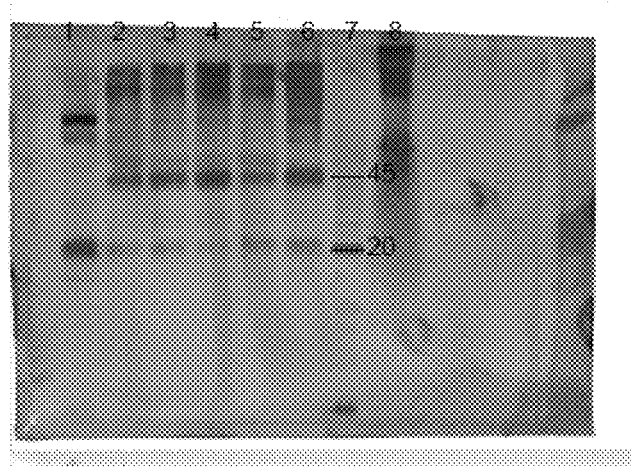

The results are shown in FIG. 6. The signals correspond respectively to:

1: Mock; 2: P1-A20T; 3: P1K54G; 4: P1-Q66R; 5: P1 Tz3; 6: IYMV P1; 7: Ladder; 8: Ladder (Mock=½ empty A4K7+ ½ mixture with P1Tz3.

The P1-Q66R mutation (line 4) has the strongest effect on PSA accumulation.

Experiment 6

Mixture with IYMV P1

The conditions used correspond to those in Experiment 7 above.

The results are shown in FIG. 7. The signals correspond respectively to:

1: T+; 2: Ladder; 3: D+8; 4: D+7; 5: D+6; 6: D+5; 7: D+3; 8: Mock (Mock=½ empty A4K7+½ mixture with P1Tz3).

As with P1-Tz3, the effect of IYMV on PSA accumulation is at its highest on days 5 and 6 (lines 5 and 6) after co-infiltration with the gene of interest.

Experiment 7

Yields with 100 g of Powder

FIG. 8 shows the yields obtained with P120, P154, P166, P1IYMV and P1 Tz3. Quantities used in ng/Western on PSA A3B with a rabbit anti-C ter antibody.

The table shows the various yields obtained, depending on the suppressor or the P1-Tz3 mutant, with an increasing range of purified PSA.

Bibliographical References

1—Voinnet et al., 1999, Proceedings of the National Academy of Sciences of the United States of America 1999; 96(24):14147-52.

2—Siré et al., Virology Journal, 2008, 5:55, p 1-12.

3—Sérémé et al., Arch. Virol., 2008, 153: p 1813-1820.

---

The invention claimed is:

1. A composition for the inoculation in a plant of agrobacteria transfected by expression vectors, in order to produce in said plant a promastigote surface antigen (PSA) or a PSA derivative, by deletion or by mutation, characterised in that it comprises
   a) agrobacteria transfected by at least one expression vector, comprising a nucleotide sequence insert that codes for said PSA or a PSA derivative, and upstream of said nucleotide sequence and downstream of a promoter of said nucleotide sequence a nucleotide sequence that codes for a *Leishmania* secretion/excretion signal peptide (SP) and
   b) agrobacteria transfected by a plurality of expression vectors, each comprising at least one nucleotide sequence insert that codes for proteins having a silencing suppressor effect.

2. Composition according to claim 1, characterised in that the nucleotide sequence that codes for the signal peptide comprises the polynucleotide sequence set forth in any of SEQ ID NOS: 14-16, coding respectively for the signal peptide of the PSA of *L. mexicana, L. infantum* (encoded by the IJ11 gene) or *L. amazonensis* (encoded by the cDNA clone A3B).

3. Composition according to claim 1, characterised in that the sequences inserted in the expression vectors in b) code for proteins having a silencing suppressor effect expressed by rice yellow mottle virus (RYMV), Imperata yellow mottle virus (IYMV), beet western yellows virus (BWYV) or tomato ringspot virus (TRSV), or mutants thereof.

4. Composition according to claim 3, characterised in that the nucleotide sequences code for a rice yellow mottle virus (RYMV) or Imperata yellow mottle virus (IYMV) P1 suppressor protein, which is also responsible for cell-to-cell movement in the plant, or a mutant of the P1 protein expressed by a nucleic acid sequence in which a wild-type codon has been modified.

5. Composition according to claim 4, characterised in that the nucleic acid sequences modified by mutation comprise wild-type sequences of rice yellow mottle virus (RYMV) P1 of Tz3 isolate in which the GCC codon in position 58 has been replaced by the ACC codon, and/or the AAG codon in position 160 has been replaced by the GGG codon and the CAG codon in position 196 by the GAC codon, said mutant nucleic acids being designated by P1-A20T, P1-K54G, P1-Q66R, P1-Q110D and those including the first three mutations by P1 A20T-K54G-Q66R.

6. Composition according to claim 5, characterised in that the nucleotide sequences modified by mutation code for mutant proteins compared to wild-type rice yellow mottle virus (RYMV) P1 of Tz3 isolate in which Ala in position 20 has been replaced by Thr, Lys in position 54 by Gly, Gln in position 66 by Arg and Gln in position 110 by Asp.

7. Composition according to claim 1, characterised in that the nucleotide sequence inserted in vector a) comprises one of sequences SEQ ID NO: 1-5 and 11.

8. Composition according to claim 7, characterised in that said nucleotide sequences are capable of coding for PSAs of sequences SEQ ID NO: 6-10 and 12.

9. Composition according to claim 1, characterized in that the nucleotide sequence inserted in vector a) comprises the IJ11 gene of *L. infantum* of sequence SEQ ID NO: 11, which codes for the LiPSA 50s protein of sequence SEQ ID NO: 12, or of the cDNA clone A3B of *L. amazonensis* of sequence SEQ ID NO: 13.

10. Composition according to claim 7, characterised in that the nucleotide sequence inserted in vector a) includes at least one mutation.

* * * * *